United States Patent
Kwok et al.

(10) Patent No.: US 11,326,169 B2
(45) Date of Patent: May 10, 2022

(54) METHOD OF PRODUCING AN APTAMER AND USES THEREOF

(71) Applicant: City University of Hong Kong, Kowloon (HK)

(72) Inventors: Chun Kit Kwok, Kowloon (HK); Chun Yin Chan, Chai Wan (HK)

(73) Assignee: City University of Hong Kong, Kowloon (HK)

( * ) Notice: Subject to any disclaimer, the term of this patent is extended or adjusted under 35 U.S.C. 154(b) by 27 days.

(21) Appl. No.: 16/706,978

(22) Filed: Dec. 9, 2019

(65) Prior Publication Data

US 2021/0171950 A1 Jun. 10, 2021

(51) Int. Cl.
*C12N 15/115* (2010.01)
*C12N 15/10* (2006.01)

(52) U.S. Cl.
CPC ........ *C12N 15/115* (2013.01); *C12N 15/1048* (2013.01); *C12N 2310/16* (2013.01); *C12N 2310/50* (2013.01)

(58) Field of Classification Search
None
See application file for complete search history.

(56) References Cited

PUBLICATIONS

Umar et al., NAS vol. 48(18):10125-10141,2020.*
Chan et al., Angew. Chem. Int. Ed., vol. 59:5293-5297, 2020.*

* cited by examiner

*Primary Examiner* — Sean McGarry
(74) *Attorney, Agent, or Firm* — Renner Kenner Greive Bobak Taylor & Weber

(57) ABSTRACT

A method of producing an aptamer selectively binding a non-canonical structure of a target nucleic acid molecule includes the steps of: incubating a plurality of nucleic acid sequences with an enantiomer of the non-canonical structure under suitable conditions to obtain one or more candidate nucleic acid sequences binding to the enantiomer of the non-canonical structure, purifying and amplifying the one or more candidate nucleic acid sequences; repeating said incubating, purifying and amplifying steps for a predetermined number of cycles under different conditions; and producing an enantiomer for selected amplified candidate nucleic acid sequence to obtain the aptamer capable of selectively binding the non-canonical structure of the target nucleic acid molecule. An aptamer selectively binding to a non-canonical structure of a nucleic acid molecule or its enantiomer, the aptamer comprising a sequence of SEQ ID NO: 11; as well as uses of the aptamer or its enantiomer.

13 Claims, 18 Drawing Sheets

Specification includes a Sequence Listing.

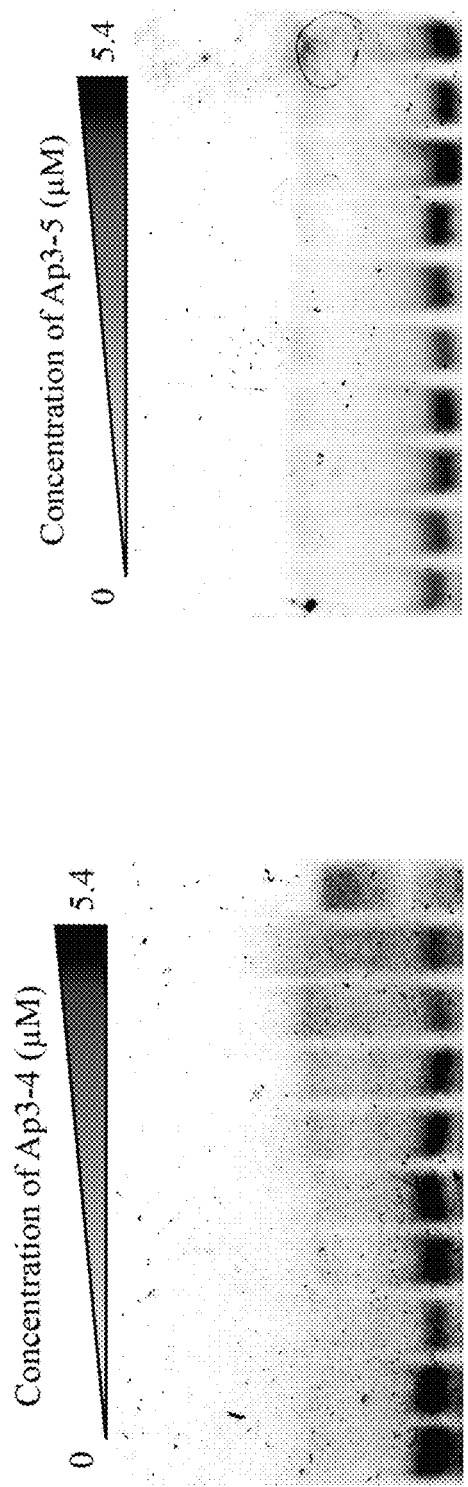
Figure 8A
Figure 8B
Figure 8C

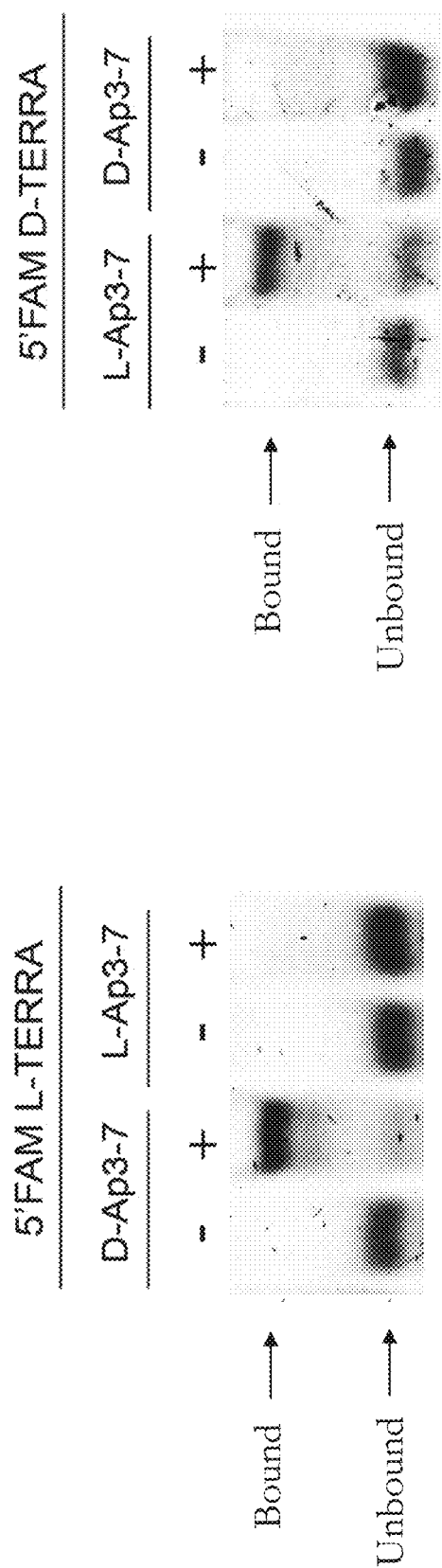

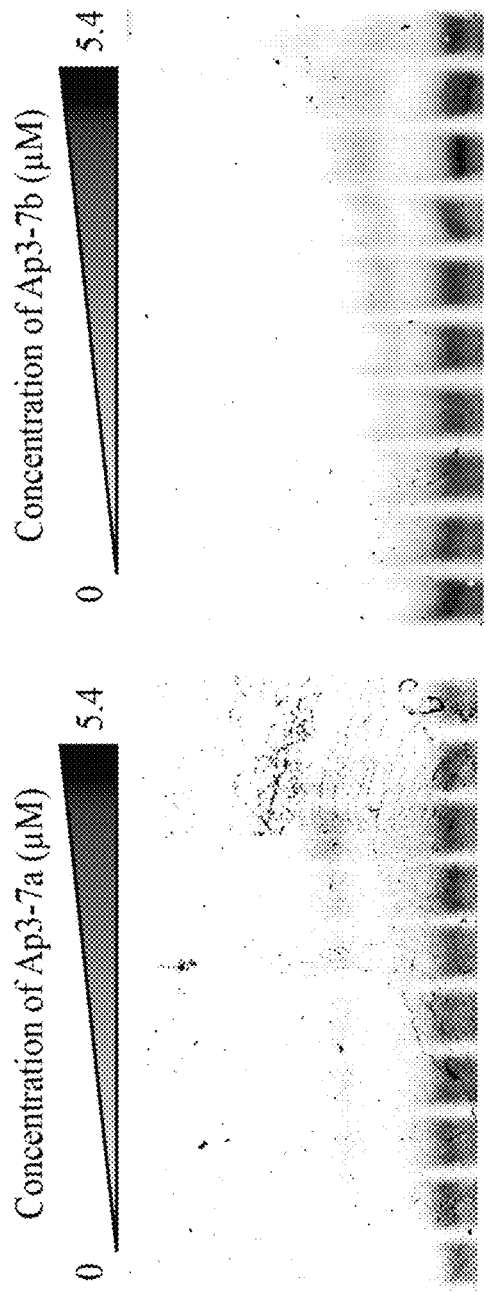
Figure 13A
Figure 13B
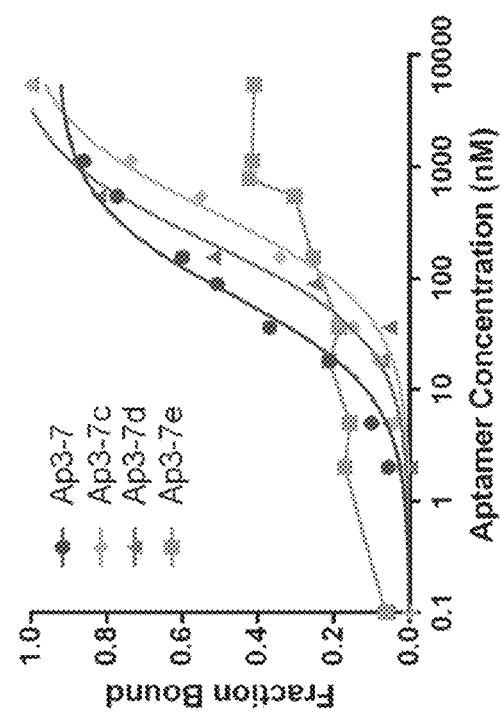
Figure 14

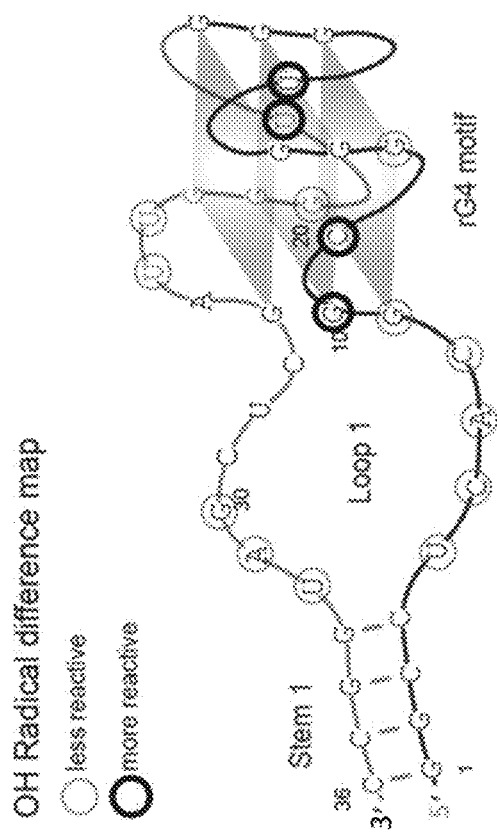
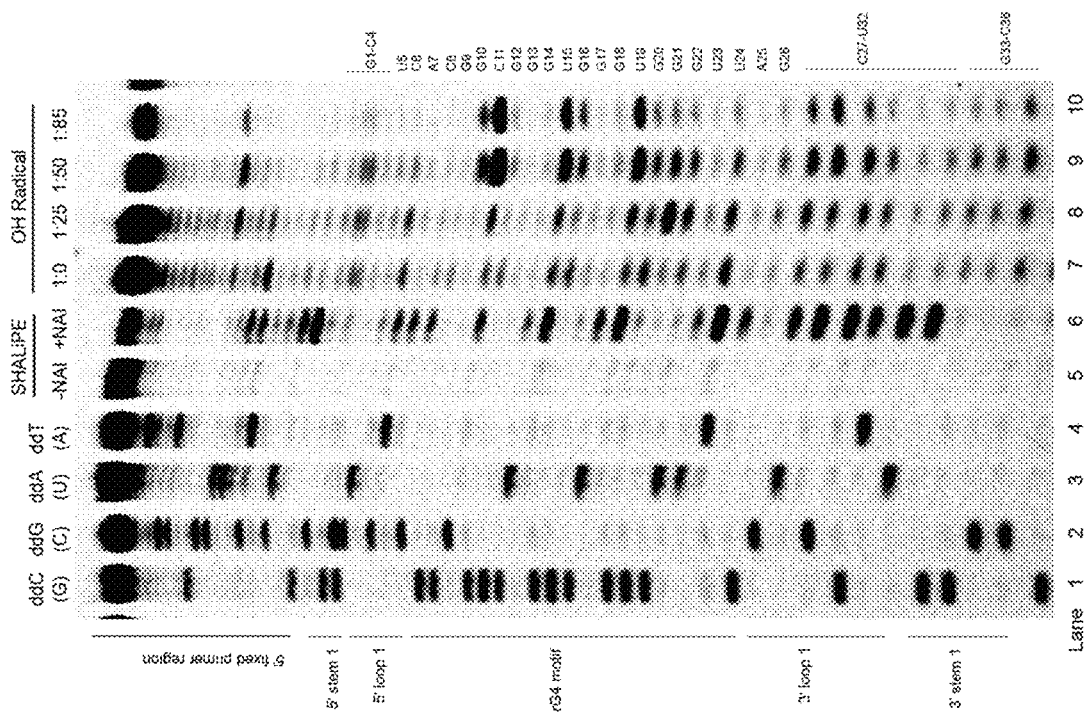
Figure 18B
Figure 18A

US 11,326,169 B2

METHOD OF PRODUCING AN APTAMER AND USES THEREOF

The Sequence Listing file entitled "sequencelisting" having a size of 6,982 bytes and a creation date of Dec. 9, 2020, that was filed with the patent application is incorporated herein by reference in its entirety.

TECHNICAL FIELD

The invention relates to a method of producing an aptamer, and particularly, although not exclusively, a method of producing an aptamer for binding a non-canonical structure of a nucleic acid molecule. The invention also relates to said aptamer and use thereof.

BACKGROUND

Guanine (G)-rich DNA or RNA sequences that contain intimate G-tracts can self-assemble into non-canonical, polymorphic, four-stranded structure motifs known as G-quadruplexes (dG4s or rG4s). Over the years, G4s have been reported to regulate diverse biological processes including gene expression, RNA metabolism, and associated with diseases such as neurological diseases and cancers.

The diverse structural conformation and biological importance of G4s have urged the development of chemical and molecular tools with higher sensitivity and specificity. Among all, small molecule ligand is the major approach to detect G4 formation and interfere G4-mediated processes. While many G4-specific ligands can distinguish G4s with other structural motifs such as duplex or single-stranded DNA/RNA, only a few ligands are known to distinguish among G4s. Similarly, strategies using peptide/protein to bind/target G4 have been gaining attention recently, however, only a limited cases have been demonstrated to have the potential to distinguish among G4s.

On the other hand, L-RNA aptamers (termed as spiegelmers), composed of unnatural L-RNA nucleotides, have been developed for proteins, and to canonical RNA structure motifs such as RNA stem-loops, achieving specific binding to structured D-RNA through pure tertiary interactions due to their enantiomeric difference.

Accordingly, there is still a need to develop a method of identifying or producing suitable aptamers for binding a target nucleic acid molecule, especially those capable of binding to non-canonical nucleic acid structure motifs.

SUMMARY OF THE INVENTION

It is an object of the invention to address the above needs, to overcome or substantially ameliorate the above disadvantages or, more generally, to provide an aptamer that binds to non-canonical structure motifs with promising affinity and specificity.

It is also an object of the invention to provide an aptamer that is capable of interfering with and inhibiting RNA-protein or RNA-peptide interactions, particularly interaction between a gene of interest and a protein.

In accordance with a first aspect of the invention, there is provided a method of producing an aptamer selectively binding a non-canonical structure of a target nucleic acid molecule, comprising the steps of:

a) providing an enantiomer of the non-canonical structure;

b) incubating a plurality of nucleic acid sequences with the enantiomer of the non-canonical structure under suitable conditions to obtain one or more candidate nucleic acid sequences binding to the enantiomer of the non-canonical structure, purifying and amplifying the one or more candidate nucleic acid sequences, wherein step b) is repeated for a predetermined number of cycles under different conditions; and c) producing an enantiomer for at least a part of each amplified candidate nucleic acid sequence to obtain the aptamer capable of selectively binding the non-canonical structure of the target nucleic acid molecule.

In another aspect of the present invention, there is provided an aptamer or its enantiomer for selectively binding a non-canonical structure of a target nucleic acid molecule. Preferably, the aptamer has a sequence of SEQ ID NO: 11.

In a further aspect, there is provided use of said aptamer or its enantiomer in binding with a G-quadruplex structure of an RNA molecule.

In a further aspect, there is provided use of said aptamer or its enantiomer in interfering with a RNA G-quadruplex structure-peptide or RNA G-quadruplex structure-protein interaction.

BRIEF DESCRIPTION OF THE DRAWINGS

Embodiments of the invention will now be described, by way of example, with reference to the accompanying drawings in which:

FIG. 7B is the binding curve of FIG. 7A, with the 10 nM-1000 nM region zoomed in;

FIG. 8A is an electrophoretic mobility shift assay (EMSA) of Ap3-4 with TERRA rG4;

FIG. 8B is an electrophoretic mobility shift assay (EMSA) of Ap3-5 with TERRA rG4;

FIG. 8C is an electrophoretic mobility shift assay (EMSA) of Ap3-6 with TERRA rG4;

FIG. 10A shows the enantiomeric specificity of D-Ap3-7 towards L-TERRA rG4;

FIG. 10B shows the enantiomeric specificity of L-Ap3-7 towards D-TERRA rG4;

FIG. 13A is an electrophoretic mobility shift assay (EMSA) of Ap3-7a with L-TERRA rG4;

FIG. 13B is an electrophoretic mobility shift assay (EMSA) of Ap3-7b with L-TERRA rG4;

FIG. 14 shows the binding curves of Ap3-7 mutants towards TERRA rG4;

FIG. 18A shows a hydroxyl radical footprinting of Ap3-7ext upon TERRA rG4 addition;

FIG. 18B shows an OH radical difference map of Ap3-7 (SEQ ID NO. 19)ext;

DETAILED DESCRIPTION OF EMBODIMENT

Figure 1:
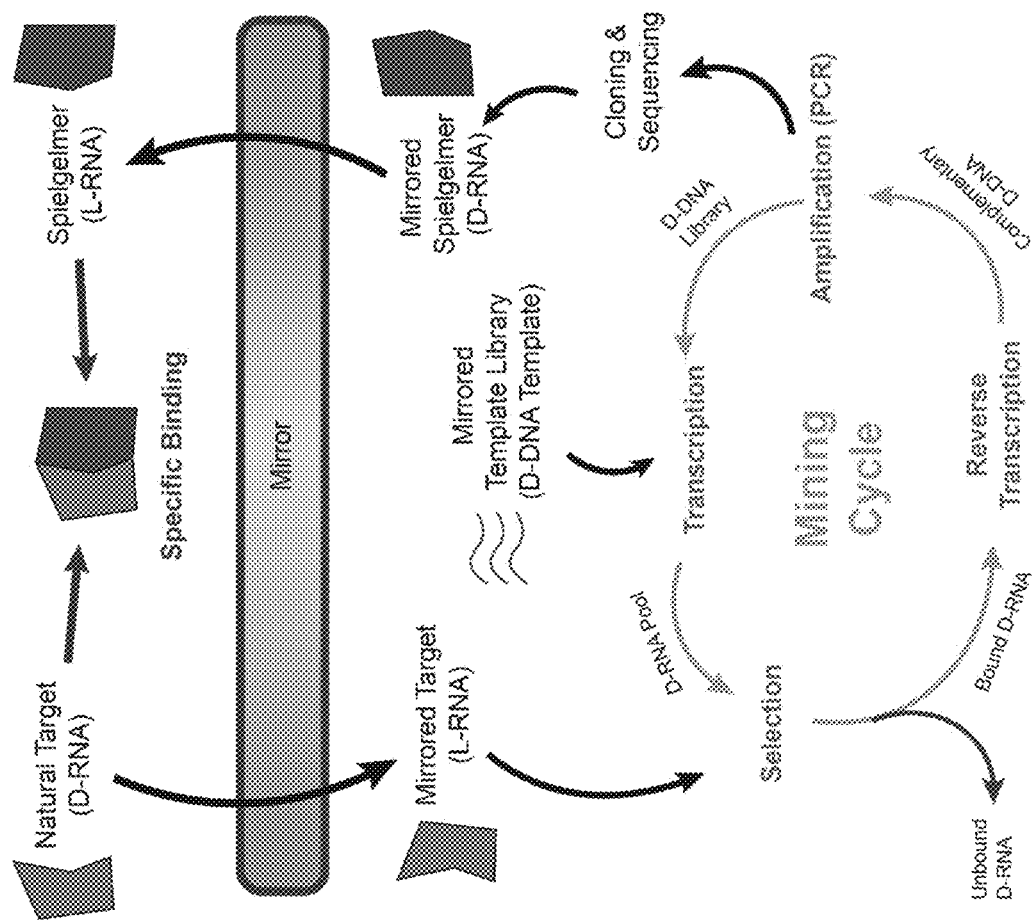
FIG. 1 is a schematic diagram showing a method of fabricating an aptamer for binding a non-canonical structure in accordance with one embodiment of the invention.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

The present invention pertains to a method of identifying or producing an aptamer that is capable of selectively binding a non-canonical structure of a target nucleic acid molecule. The term "aptamer" as used herein refers to a nucleic acid sequence that can bind to at least a part of a target nucleic acid molecule which may be a DNA or RNA molecule. The aptamer may be naturally occurring or artificially synthesized. In the present invention, the aptamer is preferably artificially synthesized based on the method as described herein, and has a length of about 20 to about 100 nucleotides, about 30 to about 80 nucleotides, or about 35 to about 40 nucleotides.

The term "non-canonical structure" as used herein refers to a part of a secondary structure of a nucleic acid molecule. Said part of the secondary structure involves interactions between non-standard (or termed non-canonical) base pairs such as hydrogen bonds between base pairs, interactions between C-H group and oxygen or nitrogen atom, and the like. In contrast, standard (or termed canonical) base pairs include base pairings of adenine and thymine (A-T), adenine and uracil (A-U), as well as cytosine and guanine (C-G) in DNA and/or RNA sequences. The non-canonical structure may be present in a target DNA or RNA sequence.

Preferably, the non-canonical structure comprises three or more successive guanine bases. The successive guanine bases may form hydrogen bonds with adjacent bases and the non-canonical structure may therefore result in a folded configuration. In an embodiment, the non-canonical structure may be a telomeric sequence containing repeating units of three or more successive guanine bases. The non-canonical structure may be a G-quadruplex structure which comprises at least four strains of successive guanine bases, and being stabilized in the presence of a monovalent cation such as potassium or sodium ion. It is believed that G-quadruplex structure takes part in immunoglobulin activity, gene synthesis, as well as pathogenies of certain diseases including cancers and neurological disorders. Accordingly, an aptamer that can bind to the G-quadruplex structure of a target nucleic acid molecule is useful in detection of normal or abnormal biological activities, and diagnosis or treatment of diseases.

Turning to the method of the present invention, it includes the following steps:

a) providing an enantiomer of the non-canonical structure;

b) incubating a plurality of nucleic acid sequences with the enantiomer of the non-canonical structure under suitable conditions to obtain one or more candidate nucleic acid sequences binding to the enantiomer of the non-canonical structure, purifying and amplifying the one or more candidate nucleic acid sequences, wherein step b) is repeated for a predetermined number of times under different conditions; and c) producing an enantiomer for at least a part of each amplified candidate nucleic acid sequence to obtain the aptamer capable of selectively binding the non-canonical structure of the target nucleic acid molecule.

Step a) provides an enantiomer, i.e. a mirror molecule, of the non-canonical structure to interact with a pool of nucleic acid sequences in step b). The enantiomer may be synthesized based on the target nucleic acid molecule or obtained from a sample. In an embodiment, step a) includes a preparation process to convert the target nucleic acid molecule particularly the non-canonical structure into an enantiomer which can help facilitate the subsequent screening procedures. In an embodiment where the target nucleic acid molecule is a D-RNA molecule bearing a non-canonical structure, an enantiomer of it, i.e. a L-RNA sequence, is used in step a). The use of enantiomer in the method, or particularly the conversion of the target canonical structure from D-RNA to L-RNA, can substantially minimize costs in the preparation of possible L-RNA candidates for screening. In other words, a pool of D-RNA sequences can be used in step b) to identify the desired D-RNA candidates binding to the enantiomer, i.e. the L-RNA sequence.

Step b) is a part of a screening procedure to identify and amplify the desired aptamer capable of binding the enantiomer of the non-canonical structure from a pool of nucleic acid sequences. In an embodiment, this step is developed based on a modified SELEX process. Particularly, the step includes a provision of a plurality of nucleic acid sequences which can be generated from various naturally occurring RNA sequences or artificially synthesized based on known sequences. Alternatively, these nucleic acid sequences can be purchased from a known biotechnology-related supplier. The plurality of the nucleic acid sequences may independently have a length of about 20 to 80 nucleotides, about 30 to about 60 nucleotides, or about 40 to 50 nucleotides.

The plurality of the nucleic acid sequences are then mixed and incubated with the enantiomer of the non-canonical structure obtained in step a) under suitable conditions for binding reaction to occur. Preferably, the non-canonical structure is labelled with a tag including, but is not limited to, a biotin tag which can be later recognized by a probe. The mixture can be incubated for about 30 minutes to 2 hours, about 30 minutes, about 1 hour or about 2 hours, in the presence of a suitable buffer solution preferably a potassium-containing buffer. After that, a probe such as magnetic beads, for example streptavidin dynabeads, is added to the mixture for isolating the bound sequences. Step b) further includes a purifying and amplifying step to release the candidate nucleic acid sequences from the enantiomer of the non-canonical structure and to amplify the candidate nucleic acid sequences for subsequent process.

The above step b) is repeated for a predetermined number of cycles under different conditions to select candidate nucleic acid sequences which have stronger affinity towards the non-canonical structure of the target nucleic acid molecules under various reaction conditions. The predetermined number of cycles may be between 5 cycles to 10 cycles, or between 3 cycles to 6 cycles.

Preferably, the step b) is repeated for at least 3 to 6 times, with the newly isolated candidate nucleic acid sequences under different reaction conditions. In other words, step b) is performed for about 4 to 7 cycles in total to obtain the optimum specific candidate sequences.

In each of the cycles, the reaction conditions including salt concentrations, incubation time and temperatures are adjusted gradually so that only candidates with a more robust affinity can survive to the next cycle. In an embodiment, the salt concentration in step b) is decreased from about 10 mM to about 1 mM in a next cycle, or from about 5 mM to about 1 mM in a particular cycle. In particular, the salt concentration in the last cycle is about 1 mM or less.

The concentration of the enantiomer of the non-canonical structure may decrease during step b) along with a decreased concentration of the nucleic acid sequences for screening. The concentration of the enantiomer of the non-canonical structure decreases by at least 50% from the concentration used in the previous cycle. The concentration of the plurality of nucleic acid sequences, or candidate nucleic acids after first or subsequent cycle, decreases by at least 30% to about 50% from the concentration used in the previous cycle. In an embodiment, the concentration of the enantiomer of the non-canonical structure in the last cycle is about 0.001 µM to about 0.01 µM, while the ratio of the concentration of the plurality of nucleic acid sequences and that of the enantiomer of the non-canonical structure is about 1:3 to about 3:1, about 1:2 to about 2:1, or about 1:1.

The mixture of the enantiomer of the non-canonical structure and the plurality of nucleic acid sequences, or the candidate nucleic acid sequences, is incubated at a temperature of 20° C. to about 40° C. for reaction. The incubation temperature may increase from about 20° C. to about 40° C. for the next cycle, or from about 22° C. to about 37° C. for the next cycle. Particularly, the temperature may increase to reach above 30° C. after the first or second cycle to identify candidates which can survive in a stringent condition. In an embodiment, the incubation temperature is 37° C. in the last cycle of step b).

Given the stringent conditions, the inventors found out that 7 cycles or less are efficient to yield the desired aptamer based on the present invention. The change of the chemical environment was proved to be not too harsh to remove too much of the nucleic acid pool, while allowing the candidate sequences to evolve efficiently. Such design allows aptamers with promising affinity to be emerged from a pool with a relatively low cost. The above repeated process is also termed as a mining process. Accordingly, the aptamer candidates obtained at the last cycle, for example at the 7th cycle, have higher affinity, higher specificity/selectivity for the target nucleic acid molecule.

In an embodiment, the enantiomer of the non-canonical structure is a L-RNA sequence, and the plurality of candidate nucleic acid sequences are D-RNA sequences. The provision of RNA sequences in D-form significantly reduces the costs incurred in the screening process of step b).

In an embodiment, the isolated candidate nucleic acid sequences can be amplified via reverse transcription to form single-stranded DNA, and then double-stranded DNA. The double-stranded DNA will then be used as the template for reproducing the candidate RNA sequences for subsequent screening cycle. It would be appreciated that other suitable amplification methods may also be applied in this invention.

In the last cycle of step b), the resultant candidate sequence may be subjected to cloning such as TA cloning, and sequencing to determine the nucleotides of the candidate sequence. Further, various modifications can be applied to the candidate sequence to obtain an optimized sequence for binding the non-canonical structure. The modifications include, but are not limited to, substitution, deletion, addition of one or more nucleotides. The modified sequences (termed as derivatives) may pose similar or the same effect in binding the non-canonical structure of the target nucleic acid sequence. Accordingly, the optimized sequence can be another candidate nucleic acid sequence according to the present invention for the similar or same effect.

In step c), the final isolated and amplified candidate nucleic acid sequence is then subjected to conversion to produce an enantiomer form. In an embodiment where the target nucleic acid bearing the non-canonical structure is a D-RNA molecule, an enantiomer of the amplified candidate D-RNA nucleic acid sequence is produced, i.e. producing a L-RNA nucleic acid sequence targeting the non-canonical structure. Accordingly, a selective aptamer particularly a L-RNA aptamer (or termed spielgelmer) is produced with enhanced stability against biological degradation.

Figure 2:
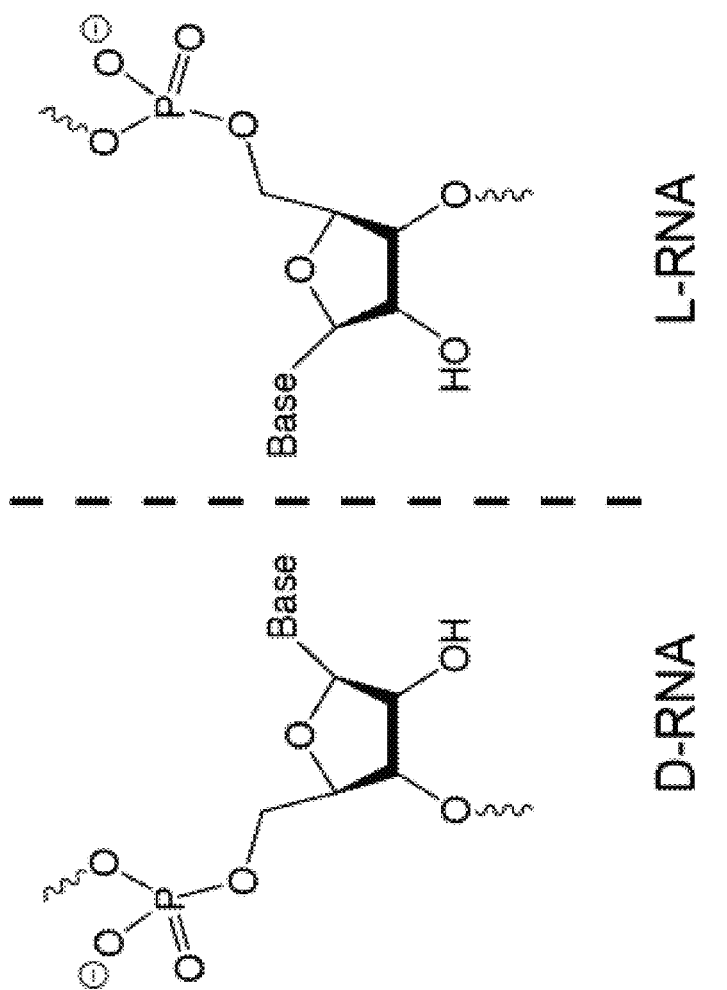
FIG. 2 shows the chemical structures of a D- and an L-RNA nucleotide, showing that these structures are enantiomers.

With reference to FIG. 1, there is illustrated an embodiment of the method of the present invention. FIG. 1 shows a schematic diagram of a modified SELEX for fabricating an aptamer for binding a non-canonical structure motif according to one embodiment of the present invention. In this embodiment, the target non-canonical structure is a D-RNA structure and therefore the desired aptamer is a L-RNA molecule. As illustrated in FIG. 2, an L-RNA nucleotide and its corresponding D-RNA nucleotide are enantiomers, i.e. they have mirrored structures of each other. As such, to generate an L-RNA aptamer specific for a D-RNA structure, the chirality of the D-RNA target is first reversed to an L-RNA structure, before employing a modified SELEX process, i.e. the step b) as described above.

In particular, first, a D-DNA template library containing random sequences is flanked with fixed primer regions and transcribed into a D-RNA pool. The pool is then selected against a mirrored L-RNA target and the bound candidates are reserved, transformed back to D-DNA and amplified by PCR.

Next, the PCR product is used for transcription of the subsequent round of mining cycle with a more stringent selection condition. After several rounds of mining, preferably seven rounds, the selected library is cloned and sequenced. The fittest candidate is then optimized and converted back to the final desired L-RNA aptamer.

Throughout the mining cycle, the RNA pool is allowed to evolve under a trend of conditions with decreasing RNA library and target concentrations, decreasing magnesium ion concentration, decreasing negative and positive selection time, increasing selection temperature and increasing washing time. The accurate increase of stringency of the conditions allows evolving a specific and affinitive speigelmer efficiently and economically.

Figure 3:
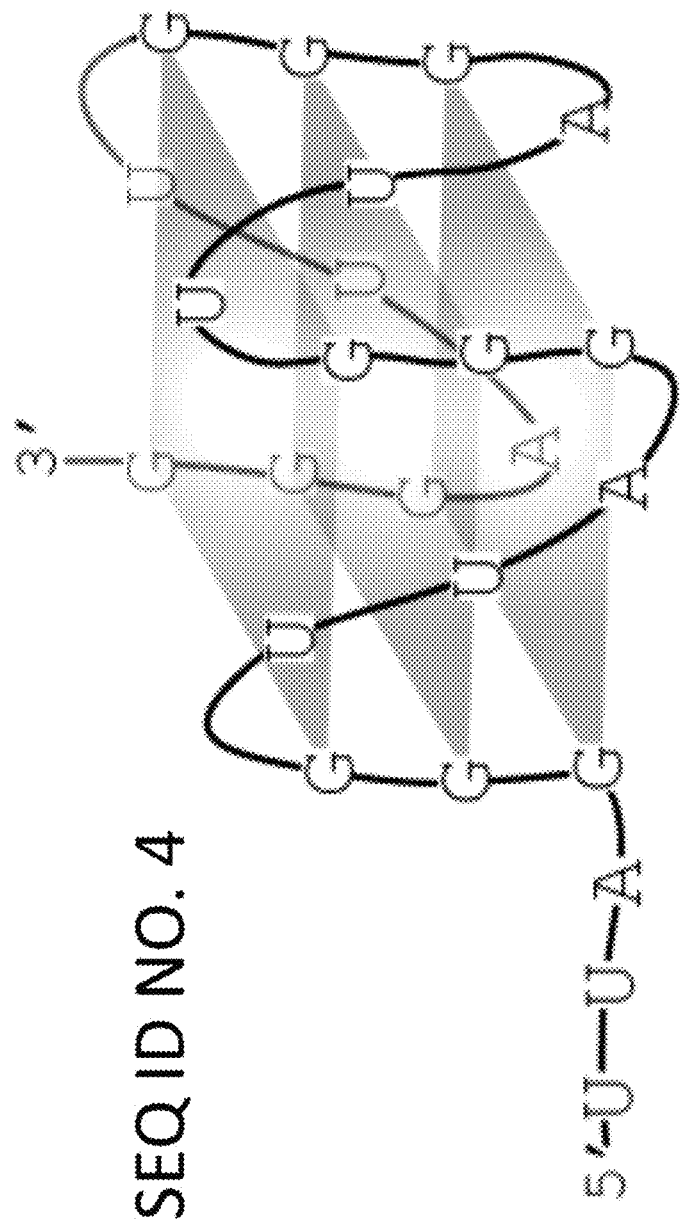
FIG. 3 shows the structure of TERRA rG4 for use in the method of FIG. 1 in accordance with one example embodiment of the invention.

FIG. 3 shows a D-telomeric repeat-containing RNA (D-TERRA) rG4 as the target in a preferred embodiment, containing 3 G-quartets and UUA loops. In this embodiment, the method further includes, prior to reverse the chirality of D-TERRA rG4, appending a 5' biotin to produce a biotin-L-TERRA rG4, as will be discussed in details in the example section. In addition, monovalent-cation-containing buffer solutions (are used throughout the mining cycle, for stabilizing the G-quadruplexes (dG4s or rG4s).

In another aspect of the present invention, there is provided an aptamer or its enantiomer for selectively binding a non-canonical structure of a target nucleic acid molecule. Preferably, the aptamer has a sequence of SEQ ID NO: 11. The aptamer may have a sequence selected from the group consisting of SEQ ID NO: 12, SEQ ID NO: 13, SEQ ID NO: 14, SEQ ID NO: 15, SEQ ID NO: 19, and an enantiomer thereof. Said aptamer has affinity towards a G-quadruplex structure and can interfere the interaction between the G-quadruplex structure and a peptide or a protein. In particular, the G-quadruplex structure has a sequence of SEQ ID NO: 4, and is preferably present in a telomeric repeat-containing RNA (TERRA) strand. Accordingly, the aptamer is a potential agent for inhibiting the binding between an enzyme such as a telomerase and the TERRA strand, thereby inducing programmed cell death of cells. It would be appreciated that the aptamer having a sequence of SEQ ID NO: 11 can be modified to add or substitute by one or more nucleotides without significantly affecting the desired binding effect.

In an embodiment where the aptamer is a RNA fragment, the aptamer has a sequence of SEQ ID NO: 19.

In an alternative embodiment where the aptamer is a DNA fragment, the aptamer has a sequence of SEQ ID NO: 6.

In a further aspect, there is provided use of the aptamer as described above in binding with a G-quadruplex structure of a RNA molecule.

In a further aspect, there is provided use of the aptamer as described above in interfering with a RNA G-quadruplex structure-protein or G-quadruplex structure-peptide interactions.

In a further aspect, there is provided a method of using the aptamer as disclosed herein for diagnosis or treatment of a disease. The aptamer may be tagged with a fluorescent label to indicate the presence of non-canonical structure of a target nucleic acid molecule in a sample for diagnosis. Alternatively, the aptamer may be used to modify a drug molecule so as to target a site containing non-canonical structure for treatment.

The examples set out below further illustrate the present invention. The preferred embodiments described above as well as examples given below represent preferred or exemplary embodiments and a skilled person will understand that the reference to those embodiments or examples is not intended to be limiting.

MATERIALS AND METHODS

Materials

All standard DNA oligonucleotides (oligos) used in the following examples were synthesized by Beijing Genomics Institute (BGI), Integrated DNA Technologies (IDT) or Genewiz, including the selection primers, M13 primers and aptamer templates. The DNA N40 library template was obtained from IDT. All D-RNA oligos and 5'FAM-labeled D-TERRA rG4 were synthesized by IDT. 5'biotinylated L-RNA TERRA rG4, 5'FAM-labeled L-RNA TERRA rG4 and 5'FAM-labeled L-RNA aptamer were ordered from Bio-Synthesis, Inc. Invitrogen's Dynabeads™ MyOne™ Streptavidin C1 was employed to retain bound RNAs. New England BioLabs (NEB)'s HiScribe™ T7 High Yield RNA Synthesis Kit, Invitrogen's SuperScript™ III (SSIII) First-Strand Synthesis System, Invitrogen's TOPO-TA Cloning Kit and Tiangen Biotech (Beijing)'s TIANprep Mini Plasmid Kit were employed for T7 in vitro transcription, reverse transcription, plasmid preparation and plasmid extraction respectively. All PCRs were carried out with NEB's QS Hot Start High-Fidelity Master Mix, except the last round where Thermo Scientific's DreamTaq Polymerase was used instead to add A-tail at the end of the double-stranded DNA (dsDNA) library for TOPO-TA cloning purpose. Trans5α chemically competent cells used for cloning were purchased from Transgen Biotech (Beijing). The RHAUS3 peptide (53-106aa, HPGHLKGREIGMWYAKKQGQKNKEAER-QERAVVHMDERREEQIVQLLNSVQAK) (SEQ ID NO: 34) used for the inhibition study was obtained from Ori-Gene.

Fluorescence Assay

Sample solutions containing 0.5 µM RNA were prepared in 150 mM LiCl/KCl, 10 mM LiCac buffer (pH 7.0) and 0.5 µM N-methyl mesophorphyrin IX (NMM) or Thioflavin T (ThT) ligand. Fluorescence spectroscopy was performed using HORBIA FluoroMax-4 and a 1-cm path length quartz cuvette (Wuxi Jinghe Optical Instrument Co.) was used with a sample volume of 100 µL.

Before the measurement, the samples (ligand not added) were denatured at 95° C. for 3 minutes and allowed to cool down at room temperature for 15 minutes. The NMM samples were excited at 570 nm and the emission spectra were acquired from 600 to 750 nm. ThT samples were excited at 425 nm and scanned from 440 to 700 nm instead. Data were collected every 2 nm at 25° C. with 5 nm entrance and exit slit widths. Raw ligand enhanced fluorescence spectra were first blanked by the corresponding sample spectra that resembled all chemical conditions except with the absence of the ligand. The blanked spectra were then smoothed over 10 nm (5 data points). All calculations mentioned were performed in Microsoft Excel.

Electrophoretic Mobility Shift Assay (EMSA)

Twenty-microliter reaction mixtures containing 2 nM 5'FAM labeled TERRA rG4, 150 mM KCl, 1 mM MgCl$_2$, 25 mM Tris-HCl (pH 7.5), 8% sucrose and varying aptamer concentrations were prepared and heated at 75° C. for 3 minutes, followed by 30° C. for 30 minutes. They were then loaded onto an 8% non-denaturing polyacrylamide gel (19:1, acrylamide:bis-acrylamide). The electrophoresis was carried out at 70 mA current for 150 minutes in ice bath.

The gel was scanned by FujiFilm FLA-9000 Gel Imager at 650 V and quantified by ImageJ. The curve fitting and $K_d$ determination was performed by Graphpad Prism using the provided one site-specific binding model.

Dideoxy Sequencing and Reverse Transcription with a 5'Cy5 Labeled Reverse Primer A 10 µL reaction mixture containing 0.5 µM of Ap3-7ext RNA, 0.5 µM 5'Cy5 labeled reverse selection primer and 1 mM dNTP mix were heated at 75° C. for 3 minutes under a buffer condition of 20 mM Tris-HCl (pH 7.5), 4 mM $MgCl_2$, 1 mM DTT, 150 mM LiCl (or KCl for reverse transcription stalling assay). For dideoxy sequencing, an additional 1 mM of corresponding ddNTP was added to replace nuclease-free water. After that, the mixture was allowed to cool down at 35° C. for 5 minutes and 100U of SSIII reverse transcriptase was added and further incubated at 50° C. for 15 minutes. Then, 1 µL of 2 M NaOH was added, and the mixture was heated at 95° C. for 10 minutes to degrade all RNA and protein. 2× RNA loading dye solution (NEB) was added to the reaction, and the sample were heated at 95° C. for 3 mins before loading to the 10% 8M urea denaturing gel. The gel was run at 90 W for 90 mins, and was scanned by FujiFilm FLA-9000 Gel Imager.

Selective 2'Hydroxyl Acylation Analyzed Lithium Ion-Mediated Primer Extension (SHALiPE)

The reaction procedures in the present example are very similar to those previously reported by the inventions in Kwok, C. K., et al., Angew. Chem. Int. Ed. 2016, 55, 8958. A 20 µL reaction mixture containing 0.25 µM Ap3-7ext RNA, 25 mM Tris-HCl (pH 7.5), 150 mM KCl and 1 mM $MgCl_2$ was first heated at 95° C. for 90 seconds, followed by a 90 second cooling at 8° C. The reaction mixture was allowed to equilibrate at 37° C. for 10 minutes and 1 µL of 2 M 2-methylnicotinic acid imidazolide (NAI) was added. The reaction was carried out for 5 minutes at 37° C. before 5 µL of 2 M DTT was added to quench the reaction. The acylated RNA was then subjected to column purification (zymo RNA clean and concentrator, NEB) and lithium ion-mediated reverse transcription. Finally, denaturing gel electrophoresis was carried out, as illustrated above.

Hydroxyl Radical Footprinting

The footprinting reaction was performed according to a reported protocol in Jain, S. S., et al., Nat. Protoc. 2008, 3, 1092. First, a 10 µL reaction mixture containing 0.75 µM Ap3-7ext RNA, 18.75/37.5/63.75 µM L-TERRA (for reaction lanes 1:25/1:50/1:85 only), 25 mM Tris-HCl (pH 7.5), 150 mM KCl and 1 mM $MgCl_2$ was heated at 75° C. for 3 minutes and allowed to incubate at 37° C. for 30 minutes. After that, 1 µL 10 mM sodium ascorbate, 1 µL of 0.3% hydrogen peroxide and 1µL of iron(II)EDTA (1 mM Fe(II)/2 mM EDTA) were added to the mixture at room temperature and the mixture was incubated for 4 minutes. Then, 1 µL 100 mM thiourea was added to the mixture to quench the reaction. Cleaved RNAs were subjected to column purification (zymo RNA clean and concentrator, NEB), followed by reverse transcription and denaturing gel electrophoresis, as illustrated above.

Non-Denaturing PAGE on Binding Specificity

The reaction mixtures contain 2 nM 5'FAM labeled target, 25 mM Tris-HCl (pH 7.5), 150 mM KCl and 1mM $MgCl_2$. In positive samples, 0.6 µM of Ap3-7 was added. The samples were heated in 75° C. for 3 minutes and incubated at 37° C. for 30 minutes. After that, they were loaded on an 8% non-denaturing PAGE and the electrophoresis was carried out in 70 mA current for 150 minutes, as illustrated above in the EMSA section.

Competitive Inhibition of D-TERRA rG4-RHAU53 Complex Formation by L-Ap3-7

L-RNA Ap3-7 and 5'FAM labelled D-RNA TERRA were heated at 75° C. for 3 minutes and cooled down separately. Then, reaction mixtures containing 2 nM 5'FAM labelled D-TERRA, 25 mM Tris-HCl (pH 7.5), 150 mM KCl and 1 mM $MgCl_2$ were prepared. Corresponding amount of L-Ap3-7 and 80 nM RHAU53 were premixed, then added to the specific samples and incubated at 37° C. for 30 minutes. The final samples were loaded onto a native PAGE (6%, 49:1), containing 40 mM KOAc, 1 mM $MgCl_2$ and 0.5×TBE (pH 8.3), and run at 30 mA for 75 minutes.

EXAMPLE 1

Preparation of a D-RNA $N_{40}$ Library

In this example, TERRA rG4 includes the non-canonical structure of the target nucleic acid molecule. Table 1 shows the sequences of the starting materials in one example of the present invention, i.e. the template for the flanked D-RNA $N_{40}$ library, the primers and a biotin-L-RNA TERRA rG4. The biotin-L-RNA TERRA rG4 was used as a biotin-labeled enantiomer of the non-canonical structure. The T7 promoter embedded is underlined.

A dsDNA library was generated by mixing 5 µM DNA N40 library template with 5 µM reverse selection primer in a 100 µL reaction volume, containing 10 U/µL SSIII reverse transcriptase, 1 mM dNTP mixture and 1× reverse transcription buffer (20 mM Tris-HCl (pH 7.5), 4 mM $MgCl_2$, 1mM DTT and 150 mM LiCl). After this template extension process, product obtained were purified by column (Zymoclean Gel DNA Recovery kit, NEB) and used as dsDNA template for 40 µL T7 in vitro transcription reaction, by following the protocol from the NEB HiScribe™ T7 High Yield RNA Synthesis Kit.

The reaction mixture was incubated at 37° C. for 3.5 hours, followed by 15 minutes after the addition of 2 U/µL Turbo DNase. 2×RNA stopping dye (NEB) was added, and the RNAs were purified by 10% denaturing polyacrylamide gel electrophoresis (PAGE). Bands with valid size were cut and crushed, then 80 µL/well extraction buffer (1× Tris-EDTA and 0.8 M LiCl) were added and the mixture was incubated at 1300 rpm at 4° C. overnight, followed by zymo RNA clean and concentrator column purification according to manufacturer's protocol.

TABLE 1

Design of selection library and target.

| Oligos | Sequences (5' to 3') | Type |
|---|---|---|
| Template for $N_{40}$ Library | TTCTAATACGACTCACTATAGGTTACCAGCC TTCACTGC($N_{40}$)GCACCACGGTCGGTCACAC (SEQ ID NO: 1-($N_{40}$)-SEQ ID NO: 2) | D-DNA |
| Forward Selection Primer | TTCTAATACGACTCACTATAGGTTACCAGCC TTCACTGC (SEQ ID NO: 1) | |
| Reverse Selection Primer | GTGTGACCGACCGTGGTGC (SEQ ID NO: 3) | |

TABLE 1-continued

Design of selection library and target.

| Oligos | Sequences (5' to 3') | Type |
|---|---|---|
| 5'Biotin L-TERRA rG4 | Biotin-UUAGGGUUAGGGUUAGGGUUAGGG (Biotin-SEQ ID NO: 4) | L-RNA |

EXAMPLE 2

Formation of G-Quadruplex

Figure 4B:
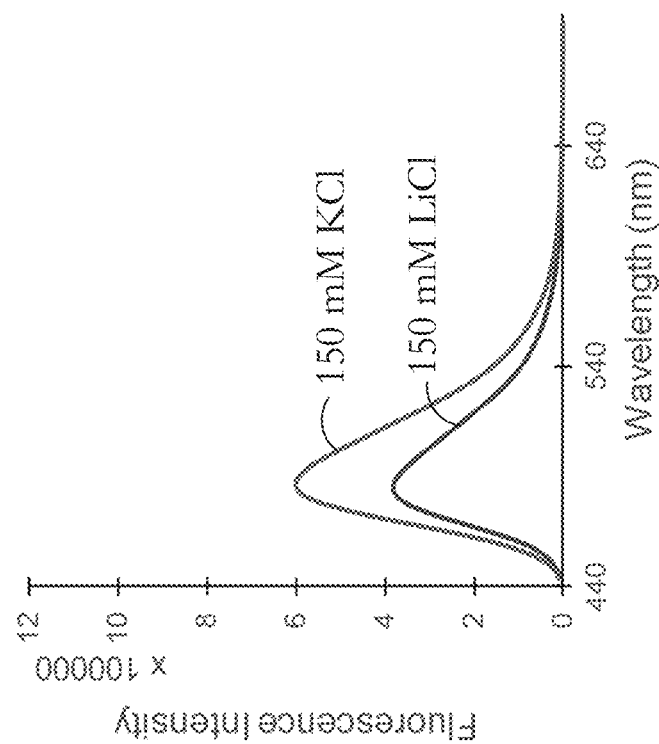
FIG. 4B is the thioflavin-T (ThT) enhanced fluorescence spectra of TERRA rG4 of FIG. 3.
Figure 4A:
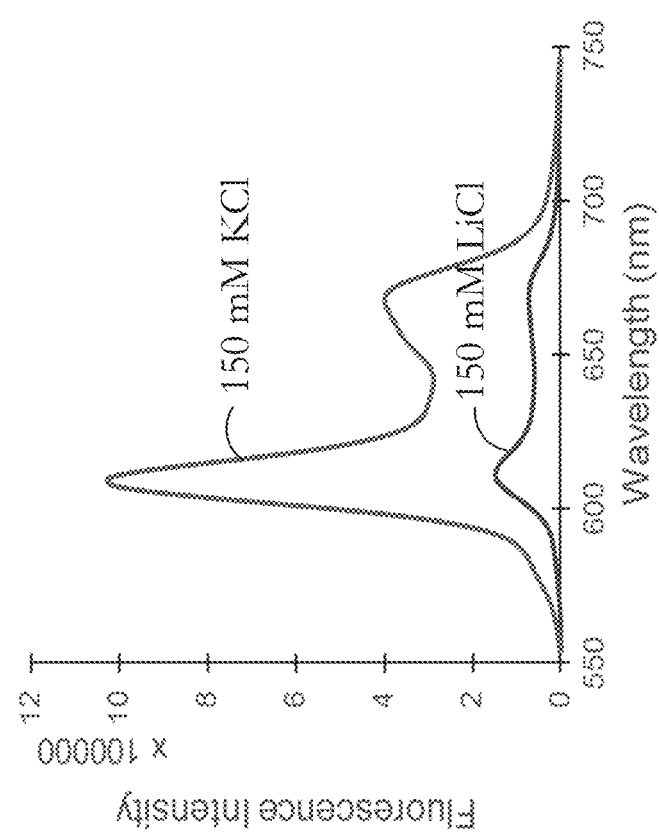
FIG. 4A is the N-methyl mesoporphyrin IX (NMM) enhanced fluorescence spectra of TERRA rG4 of FIG. 3.

With reference to FIGS. 4A and 4B, to show that the presence of biotin at the 5'end of biotin-L-TERRA rG4 did not impact on TERRA rG4 formation, rG4 fluorescent turn-on assays were performed using G4-specific ligands N-methyl mesophorphyrin IX (NMM) and Thioflavin T (ThT). Reaction mixture containing 0.5 μM L-RNA TERRA rG4 and 0.5 μM NMM showed a ca. 7- and 1.5-fold enhancement in K -containing buffer and in $Li^+$-containing buffer respectively when measured under 150 mM KCl, suggesting the formation of G-quadruplex.

EXAMPLE 3

In Vitro Selection (SELEX)

The purified RNAs in Example 1 was then subjected to a series of selection cycles, SELEX rounds, against 5'biotinylated L-RNA TERRA rG4. Table 2 shows the selection conditions with increasing stringency. Generally, each SELEX round has decreased RNA library and L-TERRA rG4 concentrations. The $MgCl_2$ concentration was decreased from 5 to 1 mM after round 4. The washing time was increased from 1 to 10 minutes after round 3. In all SELEX rounds, the concentrations of KCl and Tris-HCl (pH 7.5) were kept constant, which were 150 and 25 mM respectively. The details of negative and positive selections and washing are mentioned in materials and methods section.

To prepare for the selection, 3 mg streptavidin dynabeads were washed and activated according to Invitrogen's protocol, followed by 1 hour incubation with 0.1 mg/mL yeast tRNA at room temperature. Separately, a 300 μL reaction mixture that contains the RNA library pool, KCl, $MgCl_2$ and Tris-HCl with concentrations according to its selection round condition listed in Table 2 was prepared. This selection condition was kept unchanged throughout the negative and positive selections in each selection cycle. Next, the reaction mixture was heated at 70° C. for 3 minutes, then allowed to cool down at the selection temperature (Table 2) for 15 minutes.

Negative selection was first carried out with the addition of 1 mg prepared dynabeads to the mixture. The mixture was incubated at 300 rpm, and the corresponding temperature and negative selection time (items 4 & 7 of Table 2). The supernatant was extracted and used directly for positive selection. For the positive selection step, specific amount of 5'biotinylated L-RNA TERRA rG4 was added to the reaction mixture, reaching its final concentration (item 3 of Table 2) and allowed to incubate at 300 rpm for 30 minutes (5 minutes for the last round). After that, 2 mg of the prepared dynabeads were added to the system and allowed the incubation to continue for another 30 minutes. The supernatant was discarded and 600 μL fresh washing buffer with the same concentrations of KCl, $MgCl_2$ and Tris-HCl was added to the dynabeads, pipette mixed and allowed to incubate for the stated washing time (item 6 of Table 2). The washing step was repeated 5 times before the bound RNAs were eluted with 250 μL of 25 mM NaOH and 1 mM EDTA.

Column purification (zymo RNA clean and concentrator) was carried out after the elutate was neutralized by 5 μL of 1M Tris-HCl (pH 7.5). The purified RNAs were reversed transcribed in a 60 μL reaction mixture, containing 10 U/μL Superscript III reverse transcriptase, 1 mM dNTP mixture and 1× reverse transcription buffer (20 mM Tris-HCl (pH 7.5), 4 mM $MgCl_2$, 1mM DTT and 150 mM LiCl). The reaction was lasted for 15 minutes before 3 μL of 2 M NaOH was added and 10 minutes of incubation at 95° C. was used to degrade and denature the RNA and protein. Then, 15 μL 1 M Tris-HCl (pH 7.5) was added to neutralize the mixture before column purification (zymo RNA clean and concentrator, NEB).

The obtained single-stranded DNA (ssDNA) candidate was amplified by PCR with the forwards and reverse selection primers (Table 1). The number of PCR cycles chosen was listed in Table 2, and the resultant dsDNA was used for T7 in vitro transcription for the next selection round. Altogether, 7 selection rounds were performed in this example.

TABLE 2

Conditions used for the in vitro selection process.

| Selection rounds | 1 | 2 | 3 | 4 | 5 | 6 | 7 |
|---|---|---|---|---|---|---|---|
| $MgCl_2$ Concentration (mM) | 5 | 5 | 5 | 5 | 1 | 1 | 1 |
| D-RNA pool (μM) | 3.3 | 2 | 1 | 0.4 | 0.1 | 0.02 | 0.003 |
| L-RNA TERRA rG4 (μM) | 0.65 | 0.65 | 0.65 | 0.33 | 0.1 | 0.01 | 0.002 |
| Negative selection (hrs) | 2 | 2 | 2 | 1 | 1 | 1 | 1 |
| Positive selection (mins) | 30 | 30 | 30 | 30 | 30 | 30 | 5 |
| Washing (mins) | 1 | 1 | 1 | 10 | 10 | 10 | 10 |
| Temperature (° C.) | 22 | 22 | 37 | 37 | 37 | 37 | 37 |
| PCR cycles | 15 | 15 | 10 | 10 | 12 | 12 | 12 |

EXAMPLE 4

TA Cloning

The ssDNA in the 7th round was amplified by the DreamTaq DNA polymerase (Thermo Scientific), which can introduce an A-tail to its PCR product for TA cloning. The dsDNAs were ligated with the TOPO vector and cloned into Trans5α chemically competent cell (Transgen Biotech) using the TOPO-TA Cloning Kit (Invitrogen). The bacteria were grown at 37° C. for 15 hours on agar plates containing 50 μg/mL ampicillin. Individual colonies were picked and tested by colony PCR, where a small portion of bacteria was incubated with M13 forward and reverse primers, and premixed polymerase reaction mixture (Q5® Hot Start High-Fidelity Master Mix, NEB), and displayed with 2% agarose gel (120 V, 20 minutes).

Plasmids of colony with the correct PCR product size were then mini-prep by dropping the individual colony into 4 ml of LB medium with 50 μg/mL ampicillin for replication and growth. After 16 hours of incubation at 250 rpm at 37°

C., the plasmid DNA were extracted by TIANprep Mini Plasmid Kit (Tiangen) and sent to BGI for Sanger Sequencing.

Figure 5:
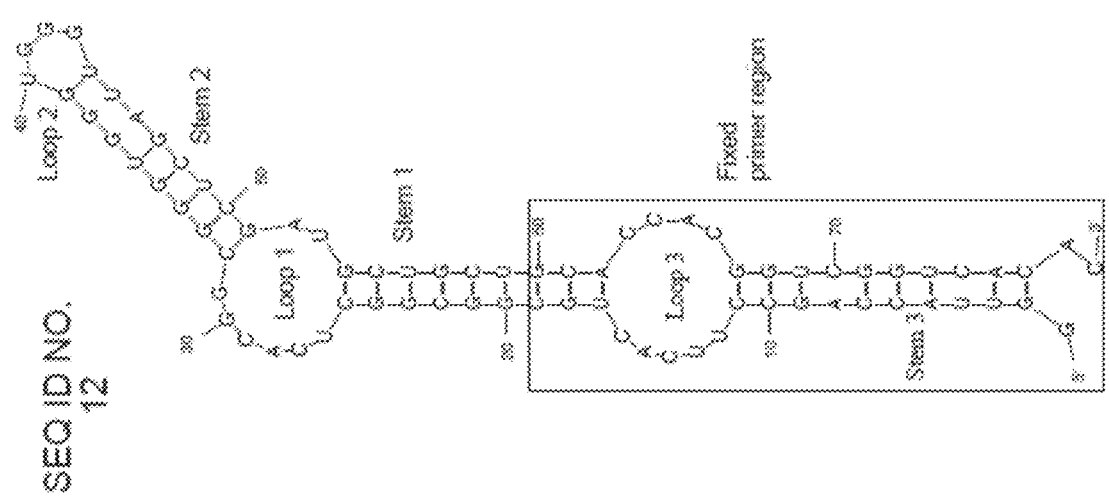
FIG. 5 is an mFold predicted structure of Ap3 fabricated using the method of FIG. 1 in accordance with one example embodiment of the invention.

Table 3 shows that 15 clones have been generated and sequenced through 7 rounds of in vitro selection for biotin-L-TERRA rG4 (Table 2). Out of the 15 clones, 10 of them (underlined in Table 3) showed the identical sequence, and this best hit (referred as aptamer candidate Ap3) was selected for further studies. Using mFold17 and as shown in FIG. 5, the secondary structure of the 78 nucleotide (nt) long Ap3 was predicted to contains 3 stems (stems 1, 2, 3), 2 internal loops and 1 hairpin loop (loops 1, 2, 3). The fixed primer region for SELEX purpose is boxed in FIG. 5.

TABLE 3

Dideoxy sequencing result.

| Colony | Sequence (5' to 3') |
|---|---|
| 1 | GCGCCAGTGCGGGGGCAGAGCGGAGGGAGAGCGCGCGTG (SEQ ID NO: 5) |
| 2 | GGCGGCTCACGGCGGGTGGGTGGGTTAGCTCGATGCTGCT (SEQ ID NO: 6) |
| 3 | GGCGGCTCACGGCGGGTGGGTGGGTTAGCTCGATGCTGCT (SEQ ID NO: 6) |
| 4 | GGCGGCTCACGGCGGGTGGGTGGGTTAGCTCGATGCTGCT (SEQ ID NO: 6) |
| 5 | GGCGGCTCACGGCGGGTGGGTGGGTTAGCTCGATGCTGCT (SEQ ID NO: 6) |
| 6 | GGCGGCTCACGGCGGGTGGGTGGGTTAGCTCGATGCTGCT (SEQ ID NO: 6) |
| 7 | GATGTCGTCGGGGTGGTGTGGGCGGGTCGCTCGTCGCAGT (SEQ ID NO: 7) |
| 8 | GGCGGCTCACGGCGGGTGGGTGGGTTAGCTCGATGCTGCT (SEQ ID NO: 6) |
| 9 | CGGCATCGAACGGGGACGTGGGAGGTGGGCGGCTGGCACT (SEQ ID NO: 8) |
| 10 | GGCGGCTCACGGCGGGTGGGTGGGTTAGCTCGATGCTGCT (SEQ ID NO: 6) |
| 11 | TATCGTGCGGGTATGCGGGTGGCGGGACGGTGGCGTGGGG (SEQ ID NO: 9) |
| 12 | GGCGGCTCACGGCGGGTGGGTGGGTTAGCTCGATGCTGCT (SEQ ID NO: 6) |
| 13 | GGCGGCTCACGGCGGGTGGGTGGGTTAGCTCGATGCTGCT (SEQ ID NO: 6) |
| 14 | GGCGGCTCACGGCGGGTGGGTGGGTTAGCTCGATGCTGCT (SEQ ID NO: 6) |
| 15 | ATCGCGGAGCGGGGCGAGGGTGCGCGGGAGGAGGGTCCT (SEQ ID NO: 10) |

To verify Ap3 RNA's binding with TERRA rG4, electrophoretic mobility shift assay (EMSA) that resembled the environment of the final selection condition were carried out with 8% native polyacrylamide gel electrophoresis (PAGE).

Figure 7B:
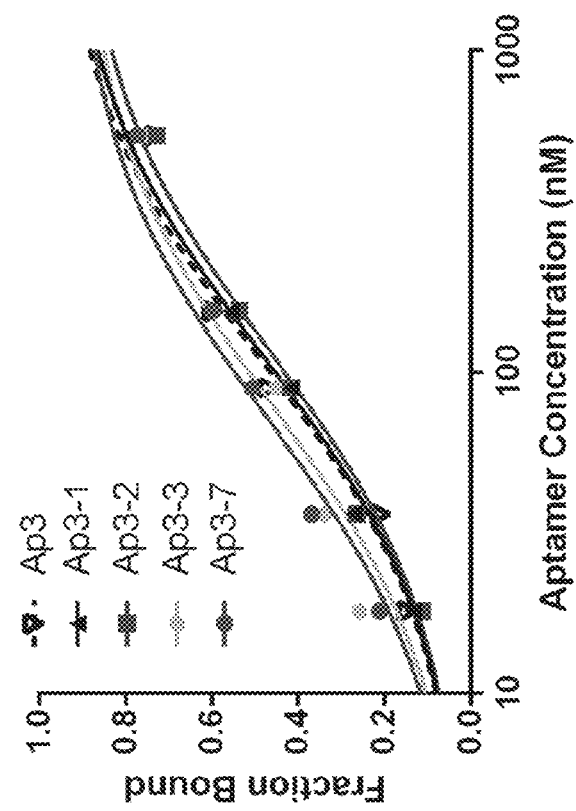
Figure 7A:
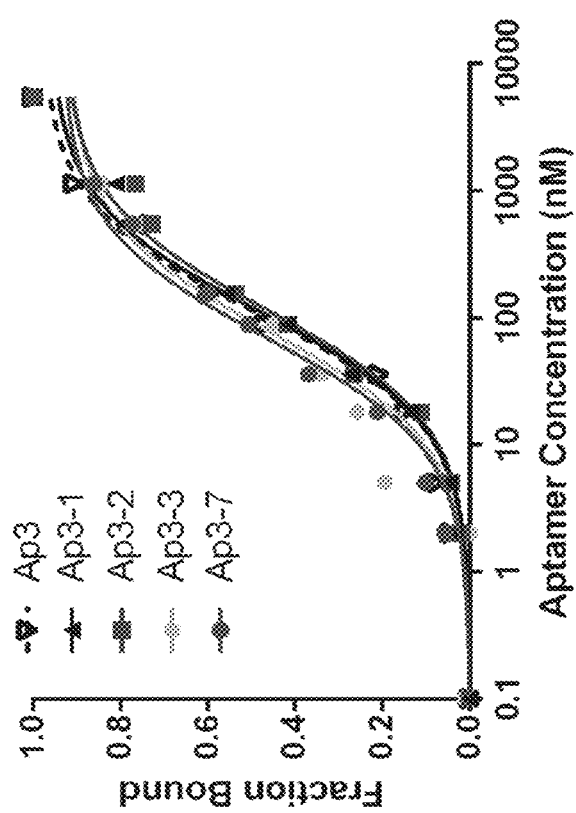
FIG. 7A shows the binding curves of Ap3 mutants towards TERRA rG4.

FIGS. 7A and 7B show the high affinity of D-Ap3 for FAM-L-TERRA rG4 observed, with a dissociation constant (Kd) of 109.7±13.8 nM, supporting the inventors' central hypothesis that RNA aptamer with opposite chirality to its target can be selected via SELEX to bind strongly to non-canonical RNA structures such as rG4.

EXAMPLE 5

RNA Sequence and Structure of D-Ap3 Towards L-TERRA rG4 Binding

To investigate the importance of the RNA sequence and structure of D-Ap3 towards L-TERRA rG4 binding, a series of mutagenesis studies were carried out and binding affinities were monitored by EMSA.

Figure 6:
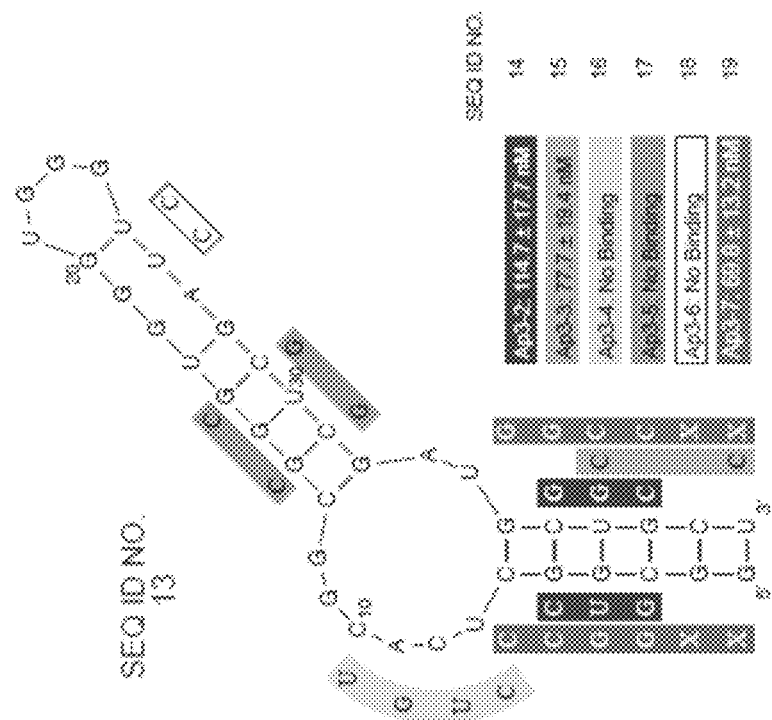
FIG. 6 shows the mFold predicted structures of Ap3-1 and mutants thereof.

First, the fixed primer regions of Ap3 (used for reverse transcription and PCR steps in RNA SELEX) were truncated. FIG. 6 shows the mFold predicted structure of this mutant, Ap3-1, with mutated sequences of its mutants. Symbol "X" in Ap3-7 indicates that the nucleotides are trimmed.

As shown in FIG. 6, it was found that the binding affinity of Ap3-1 towards TERRA rG4 (110.9±12.0 nM) was highly similar to Ap3 (FIGS. 6A and 6B), suggesting the fixed primer region is not necessary for the binding.

Second, it was evaluated whether the sequence and/or base pair structure is important in stem 1. By designing a base pair co-variation mutant (Ap3-2), it was found that a similar binding affinity was observed (114.7±17.7 nM) (FIGS. 7A and 7B). In addition, the inventors designed a base pair strengthening mutant in stem 1 (Ap3-3), and found that the binding affinity became stronger (77.68±19.4 nM) (FIGS. 7A and 7B), supporting that the base pair structure, but not sequence of stem 1 region is important for the binding.

Third, it was tested whether the sequence of loop 1 is important by performing purine to purine and pyridimine to pyridimine substitution (Ap3-4), and then examined whether the sequence and/or structure is crucial in stem 2.

FIGS. 8A to 8C show the native 8% PAGE of non-interactive Ap3 mutants, namely Ap3-4 (FIG. 7A), Ap3-5 (FIG. 7B) and Ap3-6 (FIG. 7C). All of these mutants showed single band only from 0-5.4 µM of the corresponding aptamer mutants.

It was found that the binding was abolished (FIG. 8A), indicating the loop 1 sequence is essential for the binding. Also, unexpectedly, no observable binding was found for both base pair co-variation mutant (Ap3-5) and base pair strengthening mutant (Ap3-6) (FIGS. 8B and 8C), highlighting that the sequence, but not the base pair structure of stem 2, is critical for the binding.

Finally, the inventors attempted to stabilize stem 1 by reorganizing the base pairs, while shorten the aptamer length, and designed Ap3-7 that showed the highest binding affinity (69.8±13.2 nM) to TERRA rG4 as compared to Ap3-1 to Ap3-6 (FIGS. 6), and Ap3-7 was chosen as the optimized and preferred aptamer.

As best shown in the binding curves at the 10 nM to 1000 nM region in FIG. 7B, the Kd values of the Ap3 mutants can be ordered as: Ap3-7<Ap3-3<Ap3-Ap3-1-Ap3-2.

EXAMPLE 6

Enantiomeric Specificity of Ap3-7 Towards TERRA rG4

To study whether the binding is enantiomeric-specific, EMSA was performed on D-Ap3-7 against L-TERRA rG4 and L-Ap3-7 against D-TERRA rG4.

Figures 9A, 9B:
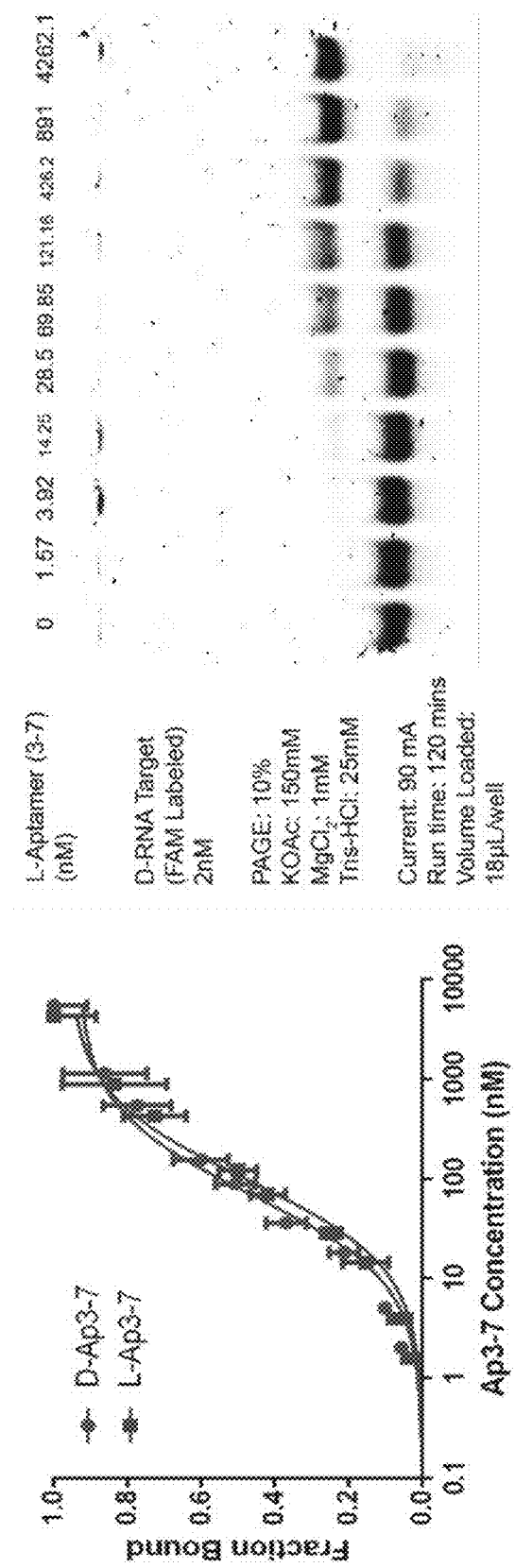
FIG. 9A shows the binding curves of L- or D-Ap3-7 towards D- or L-TERRA rG4.
FIG. 9B is an electrophoretic mobility shift assay (EMSA) of L-Ap3-7 with D-TERRA rG4.

FIG. 9A shows a curve-fitting of L- or D-Ap3-7 and FAM-D- or FAM-L-TERRA rG4 binding. The Kd values of D-Ap3-7 and L-Ap3-7 are determined to be 69.8±13.2 nM and 99.0±20.3 nM respectively. The error bars represent the SEM.

FIG. 9B shows the EMSA between 5'FAM-D-TERRA rG4 (2 nM, fixed) and L-Ap3-7 (0-5.4 µM). With increasing L-Ap3-7 concentration (from left to right), the free FAM-D-TERRA rG4 band (unbound) decreases and disappears, whereas the complex band (bound) increases and saturates.

It was revealed that their binding affinities were similar. Notably, FIGS. 10A and 10B demonstrate that no binding was observed between Ap3-7 and TERRA rG4 of same chirality under selection condition.

As shown in FIG. 10A, binding is only observed in D-Ap3-7 in the four samples containing 2 nM 5'FAM labeled L-TERRA and 0.6 µM or no Ap3-7 with the stated chirality in positive and negative samples respectively. As shown in FIG. 10B, binding is only observed in L-Ap3-7 in the four samples containing 2 nM 5'FAM labeled D-TERRA and 0.8 µM or no Ap3-7 with the stated chirality in positive and negative samples respectively.

Taken together, the results above demonstrated that the binding of Ap3-7 and TERRA rG4 is enantiomeric-specific, and more importantly, this is the first L-RNA aptamer reported that interacts with a D-rG4 structure (TERRA rG4 in this example).

EXAMPLE 7

Structural Analysis of Ap3-7 and Ap3-7 Mutants

Figure 11B:
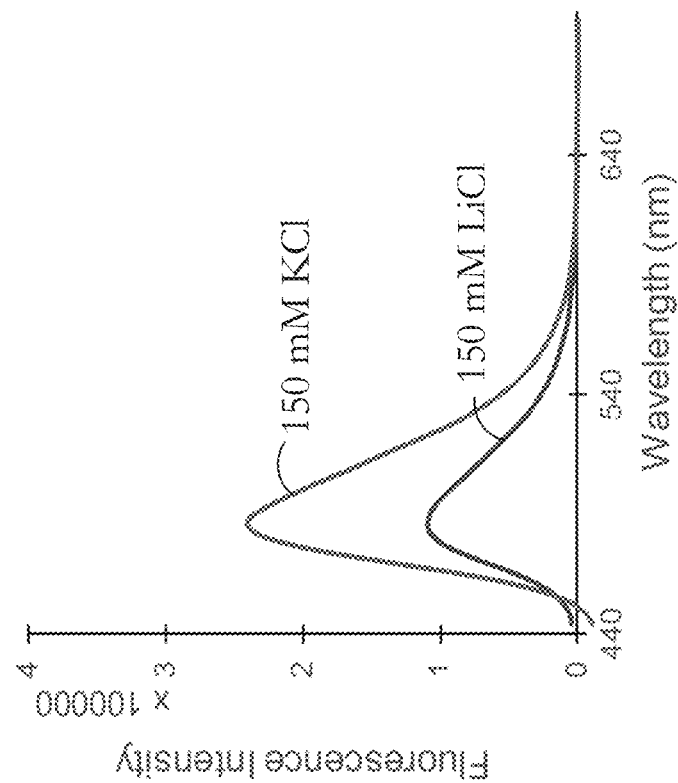
FIG. 11B is the thioflavin-T (ThT) enhanced fluorescence spectra of D-Ap3-7.
Figure 11A:
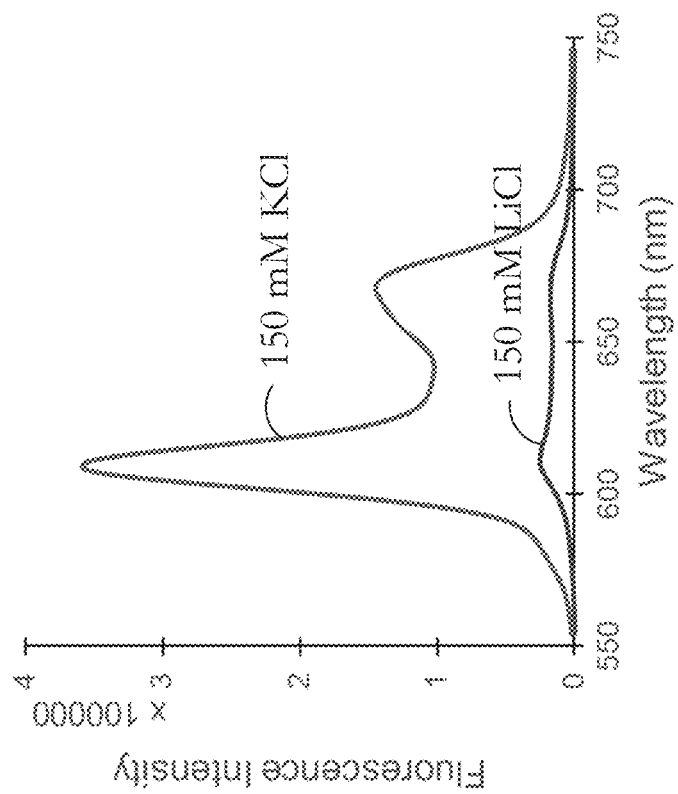
FIG. 11A is the N-methyl mesoporphyrin IX (NMM) enhanced fluorescence spectra of D-Ap3-7.

The unusual findings from Ap3-5 and Ap3-6 in stem 2 prompted the inventors to investigate the secondary structure of Ap3-7 in more details. FIGS. 11A and 11B show a ca. 14.5- and 2.2-fold enhancement in fluorescence intensity when measured under 150 mM KCl using NMM and ThT assays on Ap3-7 respectively, which suggested that Ap3-7 may contain an rG4, which cannot be predicted by mFold.

Figure 12:
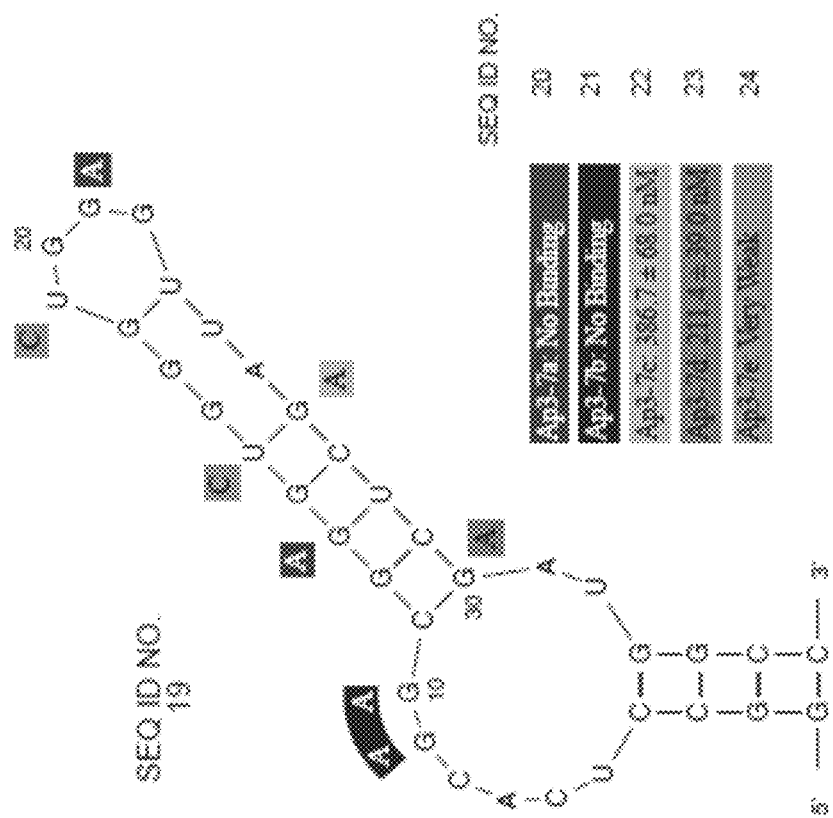
FIG. 12 is an mFold predicted structure of Ap3-7 in accordance with one example embodiment of the invention.

With reference to FIGS. 12 to 14, to further support the formation of rG4 in Ap3-7, a series of mutagenesis and binding analysis were conducted. FIG. 12 shows the mFold predicted structure of Ap3-7, with mutated sequences of its mutants. FIGS. 13A and 13B show the EMSA of two Ap3-7 mutants. FIG. 14 shows the binding curves of Ap3-7 mutants towards TERRA rG4

It was noticed that there are three GGG tracts in Ap3-7, and by designing G to A substitutions that mutate the middle Gs of 1st and 3rd G-tracts (Ap3-7a), it was found that the binding towards L-TERRA rG4 was lost (FIG. 13A), confirming the formation of rG4 in Ap3-7. The inventors also mutated G9G10 at loop 1 to A9A10, and found that the binding was also lost in this mutant (Ap3-7b)(FIG. 13B), indicating these 2 Gs are involved in the rG4 in Ap3-7. There was no observable interaction with L-TERRA rG4. All of these mutants showed single band only from 0-5.4 µM of the corresponding aptamer mutants.

Next, the inventors assessed the two single G (G26, G30), and found that mutation in G26 to A26 (Ap3-7c) caused a higher decrease in binding than G30 to A30 (Ap3-7d), as shown in FIG. 14, suggesting G26 may have a role in the rG4 formation in Ap3 and thus binding towards TERRA rG4.

Finally, the 2 potential loops (U15 and U19) in the rG4 (Ap3-7e) were mutated. As a reference, the binding curve of Ap3-7 is shown in FIG. 14, which has a Kd determined to be 69.8±13.2 nM. The Kd values of Ap3-7c and Ap3-7d were determined approximately to be 386.7±68.0 nM and 211.4±39.0 nM. The binding of Ap3-7e was too weak to be determined (fraction bound cannot approach 1 at high aptamer concentration). Ap3-7a and Ap3-7b showed no interaction with TERRA rG4 at all. These mutagenesis results from Ap3-7 mutants (Ap3-7a to Ap3-7e) also addressed the unexpected results from Ap3-5 and Ap3-6 (stem 2 base pair strengthening mutants), and provide substantial evidence that instead of having a stem 2 as predicted by mFold, Ap3-7 contains an rG4 motif (FIG. 15) that is important for TERRA rG4 binding.

Table 4 shows the sequences of oligos used in the non-denaturing PAGE. It includes a RNA hairpin control, DNA or RNA G-quadruplexes (dG4s or rG4s). Mutations made on Ap3 and Ap3-7 were underlined and bolded respectively. Particularly, Ap3, Ap3-1, Ap3-2, Ap3-3, and Ap3-7 include the same sequence fragment of CUCACGGCGGGUGG-GUGGGUUAGCUCGAUG (SEQ ID NO: 11).

TABLE 4

Sequence of aptamer mutants and targets.

| Oligos | Sequences (5'- 3') | Nucleotides |
| --- | --- | --- |
| Ap3 | GGUUACCAGCCUUCACUGCGGCGGCUCAC GGCGGGUGGGUGGGUUAGCUCGAUGCUGC UGCACCACGGUCGGUCACAC (SEQ ID NO: 12) | 78 |
| Ap3-1 | GGCGGCUCACGGCGGGUGGGUGGGUUAGC UCGAUGCUGCU (SEQ ID NO: 13) | 40 |
| Ap3-2 | GGGUCCUCACGGCGGGUGGGUGGGUUAGC UCGAUGGGCCU (SEQ ID NO: 14) | 40 |
| Ap3-3 | GGCGGCUCACGGCGGGUGGGUGGGUUAGC UCGAUGCCGCC (SEQ ID NO: 15) | 40 |
| Ap3-4 | GGCGGCCUGUGGCGGGUGGGUGGGUUAGC UCGAUGCUGCU (SEQ ID NO: 16) | 40 |
| Ap3-5 | GGCGGCUCACGGCCGCUGGGUGGGUUAGG UGGAUGCUGCU (SEQ ID NO: 17) | 40 |
| Ap3-6 | GGCGGCUCACGGCGGGUGGGUGGGUCCGC UCGAUGCUGCU (SEQ ID NO: 18) | 40 |
| Ap3-7 | GGCCUCACGGCGGGUGGGUGGGUUAGCUC GAUGGCC (SEQ ID NO: 19) | 36 |
| Ap3-7a | GGCCUCACGGCGAGUGGGUGAGUUAGCUC GAUGGCC (SEQ ID NO: 20) | 36 |
| Ap3-7b | GGCCUCACAACGGUGGGUGGGUUAGCUC GAUGGCC (SEQ ID NO: 21) | 36 |
| Ap3-7c | GGCCUCACGGCGGGUGGGUGGGUUAACUC GAUGGCC (SEQ ID NO: 22) | 36 |
| Ap3-7d | GGCCUCACGGCGGGUGGGUGGGUUAGCUC AAUGGCC (SEQ ID NO: 23) | 36 |
| Ap3-7e | GGCCUCACGGCGGGCGGGCGGGUUAGCUC GAUGGCC (SEQ ID NO: 24) | 36 |

TABLE 4-continued

Sequence of aptamer mutants and targets.

| Oligos | Sequences (5'- 3') | Nucleotides |
|---|---|---|
| Ap3-7ext | GGUUACCAGCCUUCACUGCGGCCUCACGG CGGGUGGGUGGGUUAGCUCGAUGGCCGCA CCACGGUCGGUCACAC (SEQ ID NO: 25) | 74 |
| TERRA rG4 | UUAGGGUUAGGGUUAGGGUUAGGG (SEQ ID NO: 4) | 24 |
| hTELO dG4 | TTAGGGTTAGGGTTAGGGTTAGGG (SEQ ID NO: 26) | 24 |
| hTERC rG4 | GGGUUGCGGAGGGUGGGCCU (SEQ ID NO: 27) | 20 |
| NRAS rG4 | GGGAGGGCGGGUCUGGG (SEQ ID NO: 28) | 18 |
| miR149 rG4 | AGGGAGGGACGGGGCUGUGC (SEQ ID NO: 29) | 21 |
| miR197 rG4 | CGGGUAGAGAGGGCAGUGGGAGG (SEQ ID NO: 30) | 23 |
| miR432 rG4 | UCUUGGAGUAGGUCAUUGGGUGG (SEQ ID NO: 31) | 23 |
| miR765 rG4 | UGGAGGAGAAGGAAGGUGAUG (SEQ ID NO: 32) | 21 |
| RNA hairpin | CAGUACAGAUCUGUACUG (SEQ ID NO: 33) | 18 |

To provide structural information on Ap3-7 at single nucleotide resolution, multiple structure probing assays were conducted to interrogate Ap3-7ext (extended version of Ap3-7, Table 4), which includes the fixed primer regions (FIG. 5) for reverse transcription purpose.

First, reverse transcriptase stalling (RTS) assay, recently developed by the inventors, was performed and a strong stalling signal was found only under K+condition but not in Li+ condition. Specifically, as shown in FIG. 15 and lanes 5 and 6 in FIG. 16A, the stalling location is at/near the 3'end of the last GGG tract in Ap3-7, which is a hallmark that indicates rG4 formation and its 3'most G-tract location.

Next, 2-methylnicotinic acid imidazolide (NAI) was used to measure RNA nucleotide local flexibility, and carried out Selective 2'Hydroxyl Acylation analyzed with Lithium ion-mediated Primer Extension (SHALiPE). FIG. 15 shows the proposed Ap3-7 structure based on mutagenesis and SHALiPE results, with nucleotides that have high NAI reactivity marked with asterisks, while lanes 7-10 in FIG. 16A show the SHALiPE probing of Ap3-7ext upon TERRA rG4 addition (1:0, 1:25, 1:50 & 1:85).

Figure 16B:
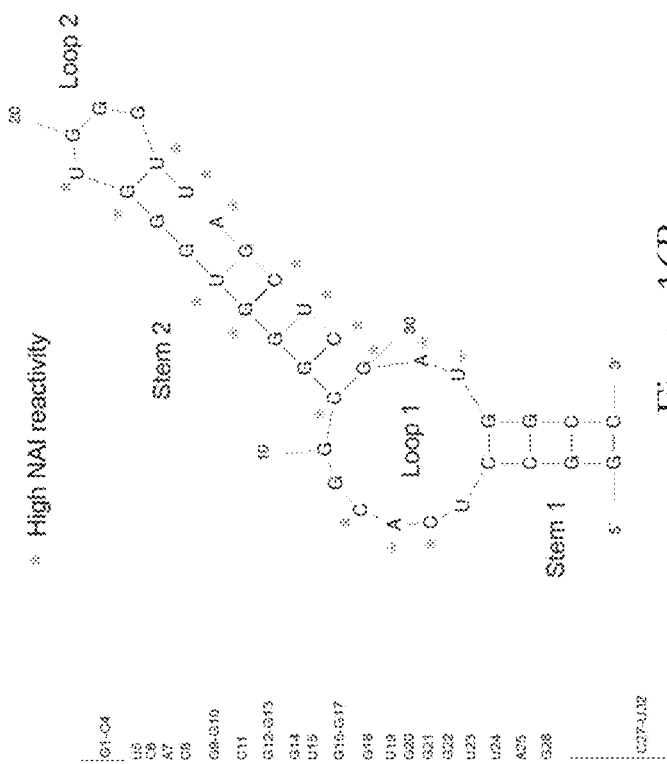
FIG. 16B illustrates the high NAI reactivity of Ap3-7 (SEQ ID NO. 19)ext.

FIG. 16B shows the predicted mFOLD structure of Ap3-7. The nucleotides with high NAI reactivity at 1:0 ratio (lane 7 in FIG. 16A) were marked with asterisks, and did not match consistently with the predicted structure. An NAI modification pattern that is consistent with the proposed Ap3-7 structure was revealed, rather than the predicted structure by mFold, as shown in FIG. 16B.

Figure 15:
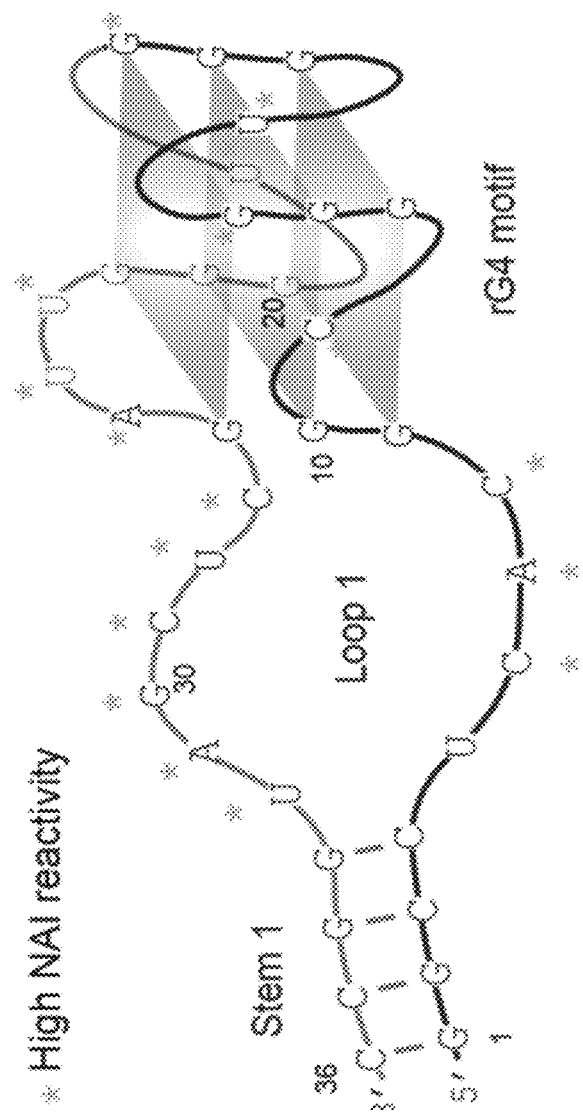
FIG. 15 illustrates the high 2-methylnicotinic acid imidazolide (NAI) reactivity of Ap3-7(SEQ ID NO. 19)
Figure 16A:
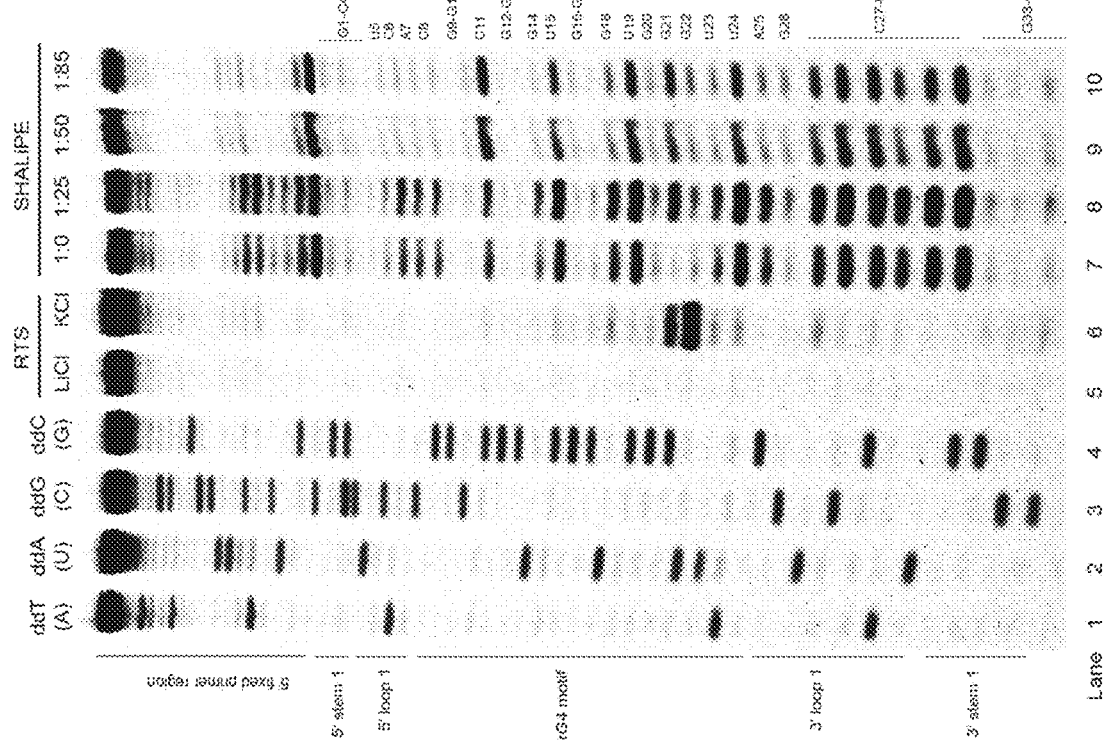
FIG. 16A shows a reverse transcriptase stalling (RTS) and SHALiPE probing of Ap3-7ext upon TERRA rG4 addition.

Notably, it was found that the nucleotides at the stem 1 are unreactive with NAI, and the nucleotides in loop 1 are highly reactive to NAI (FIGS. 15 and 16A). Consistent with SHALiPE results on rG4s in the inventors' prior study, it was observed that the loop of the rG4, as well as the 3' G of G-tracts in Ap3-7ext were highly reactive to NAI, which is a distinctive feature suggestive of rG4 formation. A closer inspection also uncovered that G26, but not G30, is unreactive to NAI, supporting the mutagenesis data that G26 is likely involved in the rG4 in Ap3-7, and its mutation inhibits the binding.

Figure 17:
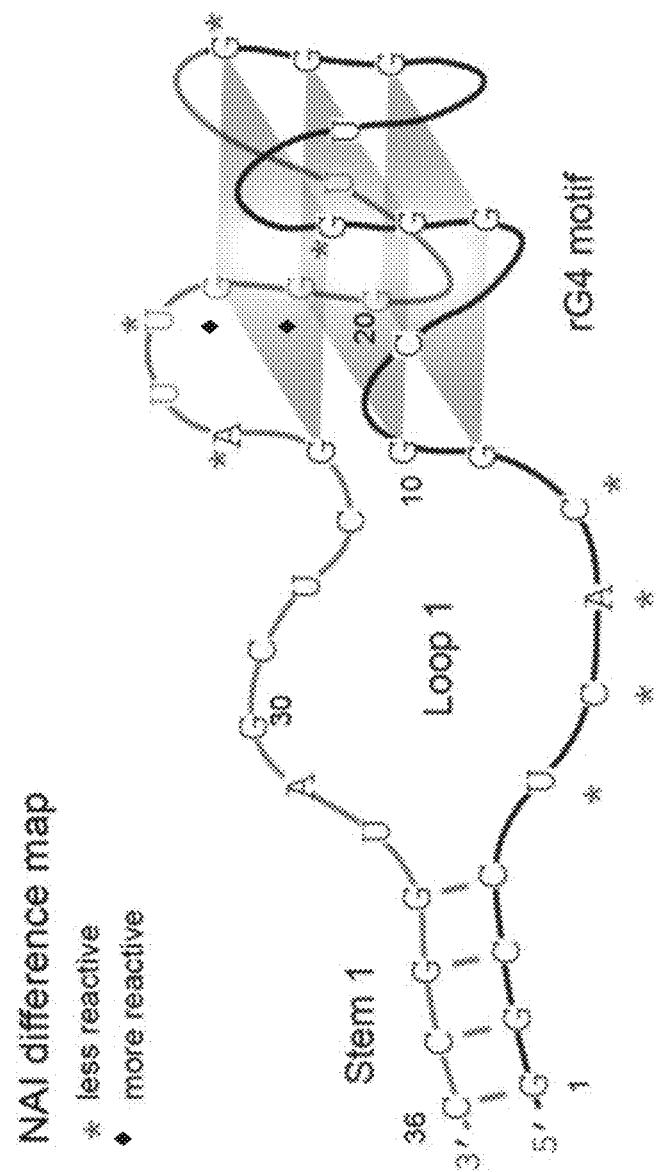
FIG. 17 shows a NAI difference map of Ap3-7(SEQ ID NO. 19)

Last, SHALiPE was performed on D-Ap3-7ext with increasing L-TERRA rG4. FIGS. 16B and 17 show the NAI reactivity difference map (comparing D-Ap3-7ext: L-TERRA rG4 between 1:0 versus 1:85). Nucleotide regions are shown with differential protection (nt 5-8, nt 14, nt 18, nt 23, nt 25) and unprotection (nt 21-22), indicating those nucleotides are involved in TERRA rG4 binding.

To extend the findings, hydroxyl-radical footprinting (HRF), which examine solvent accessibility, was carried out. FIG. 18A shows the hydroxyl radical footprinting of Ap3-7ext upon TERRA rG4 addition, in which: lanes 1-4 show the dideoxy sequencing ladder of Ap3-7ext, lanes 5 and 6 show the SHALiPE analysis of Ap3-7, with and without NAI probing, and lanes 7-10 show the hydroxyl radical probing of Ap3-7-sp upon TERRA rG4 addition (1:0, 1:25, 1:50 & 1:85). FIG. 18B shows the hydroxyl radical difference map of the proposed structure of Ap3-7. The nucleotides that were less reactive and more reactive to hydroxyl radical (comparing 1:0 and 1:85 ratio) are marked with thin and thick circles respectively.

The nucleotide regions nt 5-9, nt 12, nt 20, and nt 23-24, and nt 30-32 were found to be protected. Interestingly, nt 10-11, nt 15, nt 19 were more reactive when compared to no L-TERRA rG4 addition.

Overall, the structure probing results largely support the mutagenesis data (FIGS. 6 and 12) and the proposed structural model for Ap3-7 (FIG. 15), and reveal key nucleotides that are influenced by the TERRA rG4 binding (FIGS. 17 and 18B).

EXAMPLE 8

Specific Binding of L-Ap3-7 Towards D-TERRA rG4

Figures 19A, 19B:
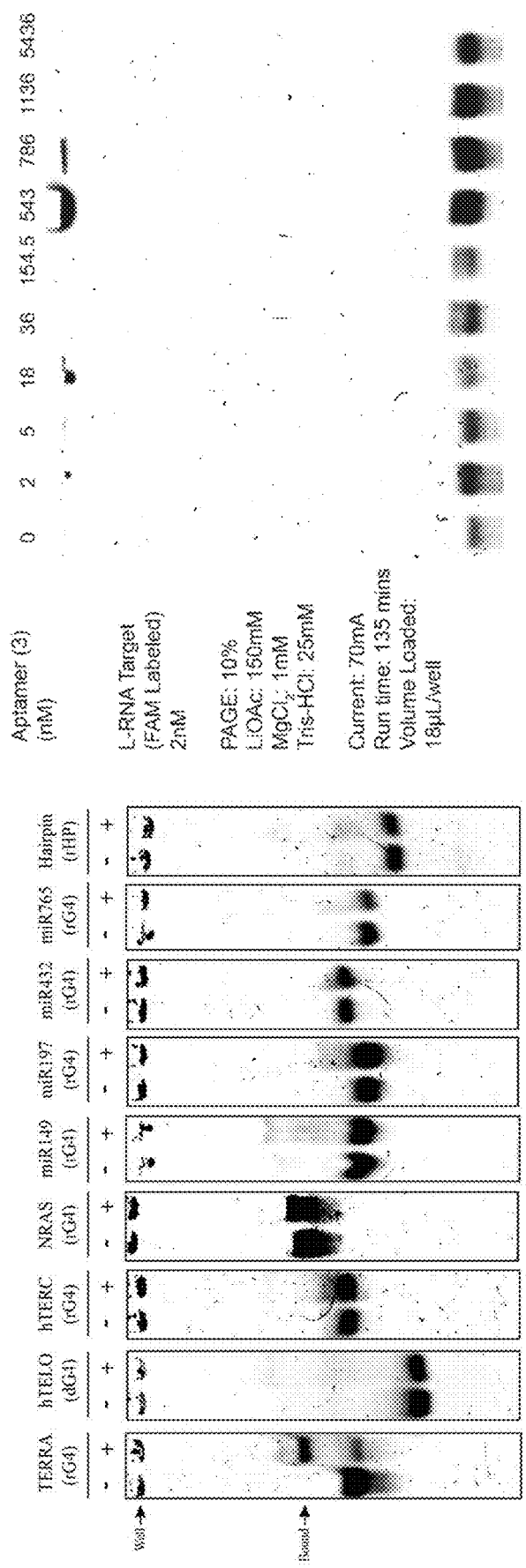
FIG. 19A shows the binding specificity of Ap3-7 towards TERRA rG4 and other constructs.
FIG. 19B shows the interaction between D-Ap3 with single-stranded L-TERRA.

To investigate whether the binding of L-Ap3-7 is specific to D-TERRA rG4, tested 8 other constructs have been tested with EMSA. FIG. 19A shows the EMSA between 5'FAM-D-TERRA rG4 or other constructs (2 nM, fixed) and L-Ap3-7 (0.6 µM L-Ap3-7). Among all, only FAM-D-TERRA rG4 interacted with L-Ap3-7 to cause a gel-shift (bound) in 8% native PAGE.

The inventors first designed an RNA hairpin (rHP) and showed no observable binding (only unbound band), suggesting the binding is G4-specific. Similar result was observed when hTELO dG4, the DNA version of TERRA rG4, was used, indicating the binding is rG4-specific.

Finally, L-Ap3-6 was tested with 6 other D-RNA constructs that were previously reported that can fold into rG4s, namely hTERC, NRAS, miRNA 149, miRNA 197, miRNA432 and miRNA765, and found no observable binding. Collectively, it has been demonstrated that the interactions between L-Ap3-7 and D-TERRA rG4 is strong and specific (FIGS. 6, 9A, 9B and 19A).

FIG. 19B demonstrates the interaction of D-Ap3 with single-stranded L-TERRA. The incubation of D-RNA Ap3-7 (prototype of Ap3-7) and L-RNA TERRA was carried out in buffer where K$^+$ ion was replaced by Li$^+$ ion that does not stabilize G-quadruplex formation. The single bands of all concentration points indicated that the present speigelmer does not interact with single-stranded TERRA.

EXAMPLE 9

Inhibition of TERRA rG4-RHAU53 Complex Formation

Figure 20A:
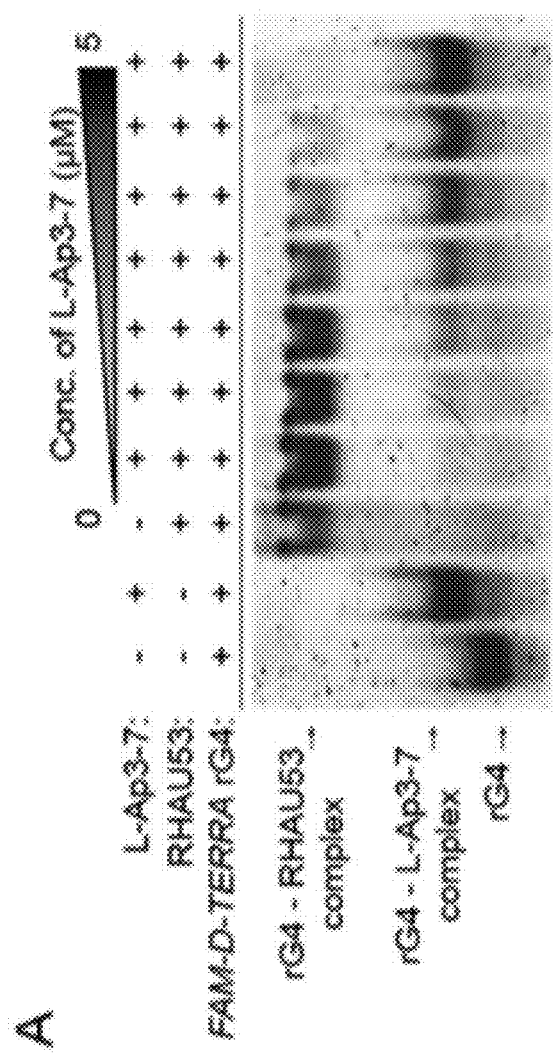
FIG. 20A is a polyacrylamide gel electrophoresis (PAGE) assay of Ap3-7 and TERRA rG4-RHAUS3, showing the inhibition of TERRA rG4-RHAUS3 binding with Ap3-7.
Figure 20B:
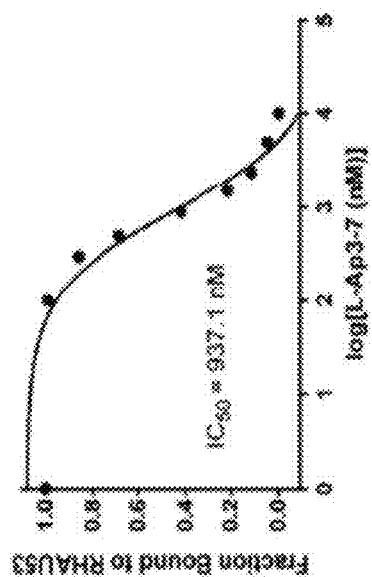
FIG. 20B shows an inhibition curve of Ap3-7 inhibiting the binding of TERRA rG4-RHAUS3.

FIG. 20A and FIG. 20B show that Ap3-7 is effective in inhibiting binding between TERRA rG4 and RHAU53 peptide.

To study if L-Ap3-7 can compete with rG4-binding protein and inhibit the D-TERRA rG4-protein complex formation, the inventors have tested it with RHAU53 peptide. Particularly, L-RNA Ap3-7 and 5'FAM labelled D-RNA TERRA were heated at 75° C. for 3 minutes and cooled down separately. Then, reaction mixtures containing 2 nM 5'FAM labelled D-TERRA, 25 mM Tris-HCl (pH 7.5), 150 mM KCl and 1 mM $MgCl_2$ were prepared. Corresponding amount of L-Ap3-7 and 80 nM RHAU53 were premixed, then added to the specific samples and incubated at 37° C. for 30 minutes. The final samples were loaded onto a native PAGE (6%, 49:1), containing 40 mM KOAc, 1mM $MgCl_2$ and 0.5 X TBE (pH 8.3), and run at 30 mA for 75 minutes.

RHAU53 is a 53-amino acid fragment (residue 53-106 of full length RHAU protein) lies in the RHAU-specific motif (RSM), and was shown to be essential for the G4 binding. Since solution with strong ionic strength inhibits the formation of TERRA rG4-RHAU53 complex, the inhibition assay was conducted in an EMSA gel with lowered K+ concentration (40 mM KOAc, 1 mM MgCl2 and 0.5× TBE). The competitive inhibition of TERRA rG4-RHAU53 complex by Ap3-7 was examined and the results in FIGS. 20A and 20B show that the formation of TERRA rG4-RHAU53 complex was largely inhibited by titrating ca. 2.4 µM of Ap3-7, with an $IC_{50}$ value 937.1±1.7 nM, in which 5'FAM-D-TERRA rG4 was fixed at 2 nM and RHAU53 was fixed at 80 nM. The results confirm that L-Ap3-7 can interfere with D-TERRA rG4-RHAU53 interactions.

Accordingly, the present invention provides a method of fabricating an L-RNA aptamer that is capable of targeting a G-quadruplex motif and selective binding to a non-canonical RNA, namely a D-TERRA rG4, by modifying the existing SELEX method and utilizing suitable reaction conditions and reagents. By using such modified method, the speigelmers produced correspond to their biological target with high affinity to their structural conformation and high selectivity towards other sequences or structures at a reasonable timescale and low cost.

The present invention is advantageous in that it provides a new and important platform for evolving and selecting spieglemers for targeting non-canonical nucleic acids structure motifs such as G-quadruplex structure. It is not only applicable for application in G-quadruplex binding/targeting studies, but also potentially applicable for biosensing, bioimaging or diagnostic applications. In addition, the aptamer sequence selected in the present invention can serve as the basis for further functionalization for targeting TERRA RNA and its biology. It is also demonstrated that the L-RNA aptamer in the present invention can compete with and inhibit RNA-peptide/protein interactions, with the unique RNA secondary structure of the L-RNA aptamer.

It will be appreciated by persons skilled in the art that numerous variations and/or modifications may be made to the invention as shown in the specific embodiments without departing from the spirit or scope of the invention as broadly described. For example, the target structure may be D-RNA structures other than D-TERRA rG4. The described embodiments of the invention should therefore be considered in all respects as illustrative, not restrictive. Any reference to prior art contained herein is not to be taken as an admission that the information is common general knowledge, unless otherwise indicated.

The invention claimed is:

1. A method of producing an aptamer selectively binding a non-canonical structure of a target nucleic acid molecule, comprising the steps of:
   a) providing an enantiomer of the non-canonical structure;
   b) incubating a plurality of nucleic acid sequences with the enantiomer of the non-canonical structure under suitable conditions to obtain one or more candidate nucleic acid sequences binding to the enantiomer of the non-canonical structure, purifying and amplifying the one or more candidate nucleic acid sequences, wherein step b) is repeated for a predetermined number of cycles under different conditions; and
   c) producing an enantiomer for at least a part of each amplified candidate nucleic acid sequence to obtain the aptamer capable of selectively binding the non-canonical structure of the target nucleic acid molecule.

2. The method in accordance with claim 1, wherein the aptamer is an RNA aptamer, and the target nucleic acid molecule is an RNA molecule.

3. The method in accordance with claim 1, wherein the non-canonical structure comprises three or more successive guanine bases.

4. The method in accordance with claim 1, wherein the non-canonical structure is a G-quadruplex structure.

5. The method in accordance with claim 1, wherein the enantiomer of the non-canonical structure is a L-RNA sequence, and the plurality of candidate nucleic acid sequences are D-RNA sequences.

6. The method in accordance with claim 1, wherein the aptamer is an L-RNA aptamer.

7. The method in accordance with claim 1, wherein the step b) is performed with a buffer solution containing potassium ions.

8. The method in accordance with claim 1, wherein the predetermined number of cycles is between 5 cycles to 10 cycles.

9. The method in accordance with claim 1, wherein the predetermined number of cycles is between 3 cycles to 6 cycles.

10. The method in accordance with claim 1, wherein salt concentration for incubation in step b) is decreased from about 10 mM to about 1 mM in a next cycle.

11. The method in accordance with claim 10, wherein the salt concentration is decreased from about 5 mM to about 1 mM in a next cycle.

12. The method in accordance with claim 1, wherein an incubation temperature for incubation in step b) is increased from about 20° C. to about 40° C.

13. The method in accordance with claim 12, wherein the incubation temperature is increased from about 22° C. to about 37° C.

* * * * *

SEQUENCE LISTING

```
<160> NUMBER OF SEQ ID NOS: 34

<210> SEQ ID NO 1
<211> LENGTH: 39
<212> TYPE: DNA
<213> ORGANISM: Artificial Sequence
<220> FEATURE:
<223> OTHER INFORMATION: Synthesized

<400> SEQUENCE: 1
ttctaatacg actcactata ggttaccagc cttcactgc                              39

<210> SEQ ID NO 2
<211> LENGTH: 19
<212> TYPE: DNA
<213> ORGANISM: Artificial Sequence
<220> FEATURE:
<223> OTHER INFORMATION: Synthesized

<400> SEQUENCE: 2
gcaccacggt cggtcacac                                                    19

<210> SEQ ID NO 3
<211> LENGTH: 19
<212> TYPE: DNA
<213> ORGANISM: Artificial Sequence
<220> FEATURE:
```

<223> OTHER INFORMATION: Synthesized

<400> SEQUENCE: 3
gtgtgaccga ccgtggtgc                                                    19

<210> SEQ ID NO 4
<211> LENGTH: 24
<212> TYPE: RNA
<213> ORGANISM: Artificial Sequence
<220> FEATURE:
<223> OTHER INFORMATION: Synthesized

<400> SEQUENCE: 4
uuaggguuag gguuaggguu aggg                                              24

<210> SEQ ID NO 5
<211> LENGTH: 40
<212> TYPE: DNA
<213> ORGANISM: Artificial Sequence
<220> FEATURE:
<223> OTHER INFORMATION: Synthesized

<400> SEQUENCE: 5
gcgccagtgc gggggcaga gcggagggag agcgcgcgtg                              40

<210> SEQ ID NO 6
<211> LENGTH: 40
<212> TYPE: DNA
<213> ORGANISM: Artificial Sequence
<220> FEATURE:
<223> OTHER INFORMATION: Synthesized

<400> SEQUENCE: 6
ggcggctcac ggcgggtggg tgggttagct cgatgctgct                             40

<210> SEQ ID NO 7
<211> LENGTH: 40
<212> TYPE: DNA
<213> ORGANISM: Artificial Sequence
<220> FEATURE:
<223> OTHER INFORMATION: Synthesized

<400> SEQUENCE: 7
gatgtcgtcg gggtggtgtg ggcgggtcgc tcgtcgcagt                             40

<210> SEQ ID NO 8
<211> LENGTH: 40
<212> TYPE: DNA
<213> ORGANISM: Artificial Sequence
<220> FEATURE:
<223> OTHER INFORMATION: Synthesized

<400> SEQUENCE: 8
cggcatcgaa cggggacgtg ggaggtgggc ggctggcact                             40

<210> SEQ ID NO 9
<211> LENGTH: 40
<212> TYPE: DNA
<213> ORGANISM: Artificial Sequence
<220> FEATURE:
<223> OTHER INFORMATION: Synthesized

<400> SEQUENCE: 9
tatcgtgcgg gtatgcgggt ggcgggacgg tggcgtgggg                             40

```
<210> SEQ ID NO 10
<211> LENGTH: 40
<212> TYPE: DNA
<213> ORGANISM: Artificial Sequence
<220> FEATURE:
<223> OTHER INFORMATION: Synthesized

<400> SEQUENCE: 10
atcgcggagc ggggcgaggg tgcgcgggag gagggtcct                              40

<210> SEQ ID NO 11
<211> LENGTH: 30
<212> TYPE: RNA
<213> ORGANISM: Artificial Sequence
<220> FEATURE:
<223> OTHER INFORMATION: Synthesized

<400> SEQUENCE: 11
cucacggcgg guggugggu uagcucgaug                                         30

<210> SEQ ID NO 12
<211> LENGTH: 78
<212> TYPE: RNA
<213> ORGANISM: Artificial Sequence
<220> FEATURE:
<223> OTHER INFORMATION: Synthesized

<400> SEQUENCE: 12
gguuaccagc cuucacugcg gcggcucacg gcgggugggu ggguuagcuc gaugcugcug       60
caccacgguc ggucacac                                                    78

<210> SEQ ID NO 13
<211> LENGTH: 40
<212> TYPE: RNA
<213> ORGANISM: Artificial Sequence
<220> FEATURE:
<223> OTHER INFORMATION: Synthesized

<400> SEQUENCE: 13
ggcggcucac ggcgggugg uggguuagcu cgaugcugcu                              40

<210> SEQ ID NO 14
<211> LENGTH: 40
<212> TYPE: RNA
<213> ORGANISM: Artificial Sequence
<220> FEATURE:
<223> OTHER INFORMATION: Synthesized

<400> SEQUENCE: 14
ggguccucac ggcgggugg uggguuagcu cgaugggccu                              40

<210> SEQ ID NO 15
<211> LENGTH: 40
<212> TYPE: RNA
<213> ORGANISM: Artificial Sequence
<220> FEATURE:
<223> OTHER INFORMATION: Synthesized

<400> SEQUENCE: 15
ggcggcucac ggcgggugg uggguuagcu cgaugccgcc                              40

<210> SEQ ID NO 16
<211> LENGTH: 40
<212> TYPE: RNA
<213> ORGANISM: Artificial Sequence
<220> FEATURE:
```

<223> OTHER INFORMATION: Synthesized

<400> SEQUENCE: 16
ggcggccugu ggcgggugggu uggguuagcu cgaugcugcu        40

<210> SEQ ID NO 17
<211> LENGTH: 40
<212> TYPE: RNA
<213> ORGANISM: Artificial Sequence
<220> FEATURE:
<223> OTHER INFORMATION: Synthesized

<400> SEQUENCE: 17
ggcggcucac ggccgcuggg uggguuaggu ggaugcugcu        40

<210> SEQ ID NO 18
<211> LENGTH: 40
<212> TYPE: RNA
<213> ORGANISM: Artificial Sequence
<220> FEATURE:
<223> OTHER INFORMATION: Synthesized

<400> SEQUENCE: 18
ggcggcucac ggcgggugggu uggguccgcu cgaugcugcu        40

<210> SEQ ID NO 19
<211> LENGTH: 36
<212> TYPE: RNA
<213> ORGANISM: Artificial Sequence
<220> FEATURE:
<223> OTHER INFORMATION: Synthesized

<400> SEQUENCE: 19
ggccucacgg cggugggug gguuagcucg auggcc        36

<210> SEQ ID NO 20
<211> LENGTH: 36
<212> TYPE: RNA
<213> ORGANISM: Artificial Sequence
<220> FEATURE:
<223> OTHER INFORMATION: Synthesized

<400> SEQUENCE: 20
ggccucacgg cgagugggug aguuagcucg auggcc        36

<210> SEQ ID NO 21
<211> LENGTH: 36
<212> TYPE: RNA
<213> ORGANISM: Artificial Sequence
<220> FEATURE:
<223> OTHER INFORMATION: Synthesized

<400> SEQUENCE: 21
ggccucacaa cggugggug gguuagcucg auggcc        36

<210> SEQ ID NO 22
<211> LENGTH: 36
<212> TYPE: RNA
<213> ORGANISM: Artificial Sequence
<220> FEATURE:
<223> OTHER INFORMATION: Synthesized

<400> SEQUENCE: 22
ggccucacgg cggugggug gguuaacucg auggcc        36

```
<210> SEQ ID NO 23
<211> LENGTH: 36
<212> TYPE: RNA
<213> ORGANISM: Artificial Sequence
<220> FEATURE:
<223> OTHER INFORMATION: Synthesized

<400> SEQUENCE: 23
ggccucacgg cgggugggug gguuagcuca auggcc                                 36

<210> SEQ ID NO 24
<211> LENGTH: 36
<212> TYPE: RNA
<213> ORGANISM: Artificial Sequence
<220> FEATURE:
<223> OTHER INFORMATION: Synthesized

<400> SEQUENCE: 24
ggccucacgg cgggcgggcg gguuagcucg auggcc                                 36

<210> SEQ ID NO 25
<211> LENGTH: 74
<212> TYPE: RNA
<213> ORGANISM: Artificial Sequence
<220> FEATURE:
<223> OTHER INFORMATION: Synthesized

<400> SEQUENCE: 25
gguuaccagc cuucacugcg gccucacggc gggugggugg guuagcucga uggccgcacc       60
acggucgguc acac                                                         74

<210> SEQ ID NO 26
<211> LENGTH: 24
<212> TYPE: DNA
<213> ORGANISM: Artificial Sequence
<220> FEATURE:
<223> OTHER INFORMATION: Synthesized

<400> SEQUENCE: 26
ttagggttag ggttagggtt aggg                                              24

<210> SEQ ID NO 27
<211> LENGTH: 20
<212> TYPE: RNA
<213> ORGANISM: Artificial Sequence
<220> FEATURE:
<223> OTHER INFORMATION: Synthesized

<400> SEQUENCE: 27
ggguugcgga ggugggccu                                                    20

<210> SEQ ID NO 28
<211> LENGTH: 18
<212> TYPE: RNA
<213> ORGANISM: Artificial Sequence
<220> FEATURE:
<223> OTHER INFORMATION: Synthesized

<400> SEQUENCE: 28
gggaggggcg ggucuggg                                                     18

<210> SEQ ID NO 29
<211> LENGTH: 21
<212> TYPE: RNA
<213> ORGANISM: Artificial Sequence
<220> FEATURE:
```

<223> OTHER INFORMATION: Synthesized

<400> SEQUENCE: 29
agggagggac gggggcugug c                                              21

<210> SEQ ID NO 30
<211> LENGTH: 23
<212> TYPE: RNA
<213> ORGANISM: Artificial Sequence
<220> FEATURE:
<223> OTHER INFORMATION: Synthesized

<400> SEQUENCE: 30
cggguagaga gggcaguggg agg                                            23

<210> SEQ ID NO 31
<211> LENGTH: 23
<212> TYPE: RNA
<213> ORGANISM: Artificial Sequence
<220> FEATURE:
<223> OTHER INFORMATION: Synthesized

<400> SEQUENCE: 31
ucuuggagua ggucauuggg ugg                                            23

<210> SEQ ID NO 32
<211> LENGTH: 21
<212> TYPE: RNA
<213> ORGANISM: Artificial Sequence
<220> FEATURE:
<223> OTHER INFORMATION: Synthesized

<400> SEQUENCE: 32
uggaggagaa ggaaggugau g                                              21

<210> SEQ ID NO 33
<211> LENGTH: 18
<212> TYPE: RNA
<213> ORGANISM: Artificial Sequence
<220> FEATURE:
<223> OTHER INFORMATION: Synthesized

<400> SEQUENCE: 33
caguacagau cuguacug                                                  18

<210> SEQ ID NO 34
<211> LENGTH: 53
<212> TYPE: PRT
<213> ORGANISM: Artificial Sequence
<220> FEATURE:
<223> OTHER INFORMATION: Synthesized

<400> SEQUENCE: 34

His Pro Gly His Leu Lys Gly Arg Glu Ile Gly Met Trp Tyr Ala Lys
1               5                   10                  15

Lys Gln Gly Gln Lys Asn Lys Glu Ala Glu Arg Gln Glu Arg Ala Val
            20                  25                  30

Val His Met Asp Glu Arg Arg Glu Glu Gln Ile Val Gln Leu Leu Asn
        35                  40                  45

Ser Val Gln Ala Lys
    50